US011371022B2

(12) United States Patent
Park et al.

(10) Patent No.: US 11,371,022 B2
(45) Date of Patent: Jun. 28, 2022

(54) BLOOD-BRAIN BARRIER ENDOTHELIAL CELLS DERIVED FROM PLURIPOTENT STEM CELLS FOR BLOOD-BRAIN BARRIER MODELS

(71) Applicant: PRESIDENT AND FELLOWS OF HARVARD COLLEGE, Cambridge, MA (US)

(72) Inventors: Tae-Eun Park, Boston, MA (US); Anna Herland, Brookline, MA (US); Edward Anthony Fitzgerald, Boston, MA (US); Donald Elliot Ingber, Boston, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 223 days.

(21) Appl. No.: 16/076,857

(22) PCT Filed: Feb. 16, 2017

(86) PCT No.: PCT/US2017/018150
§ 371 (c)(1),
(2) Date: Aug. 9, 2018

(87) PCT Pub. No.: WO2017/143049
PCT Pub. Date: Aug. 24, 2017

(65) Prior Publication Data
US 2019/0048316 A1 Feb. 14, 2019

Related U.S. Application Data

(60) Provisional application No. 62/295,693, filed on Feb. 16, 2016.

(51) Int. Cl.
*C12N 5/071* (2010.01)
*C12M 3/06* (2006.01)
*C12N 5/00* (2006.01)
*G01N 27/403* (2006.01)

(52) U.S. Cl.
CPC .......... *C12N 5/069* (2013.01); *C12M 23/16* (2013.01); *C12N 5/0062* (2013.01); *C12N 5/0068* (2013.01); *G01N 27/403* (2013.01); *C12N 2500/02* (2013.01); *C12N 2502/081* (2013.01); *C12N 2506/02* (2013.01); *C12N 2506/45* (2013.01); *C12N 2533/90* (2013.01)

(58) Field of Classification Search
CPC .... C12N 5/069; C12N 5/0062; C12N 5/0068; C12N 2500/02; C12N 2502/081; C12N 2506/02; C12N 2506/45; C12N 2533/90; C12M 23/16; G01N 27/403; G01N 33/50
See application file for complete search history.

(56) References Cited

U.S. PATENT DOCUMENTS

| 8,647,861 | B2 | 2/2014 | Ingber | |
|---|---|---|---|---|
| 2011/0104658 | A1 | 5/2011 | Prabhakarpandian | |
| 2012/0015395 | A1* | 1/2012 | Shusta | C12N 5/069 435/29 |
| 2012/0211373 | A1 | 8/2012 | El-Sayed | |
| 2014/0142370 | A1* | 5/2014 | Wong | C12N 5/069 600/36 |
| 2017/0009204 | A1* | 1/2017 | Gerecht | C12N 5/069 |

FOREIGN PATENT DOCUMENTS

| WO | 2010/040920 A2 | 4/2010 | |
|---|---|---|---|
| WO | 2011159572 A2 | 12/2011 | |
| WO | 2013/086486 A1 | 6/2013 | |
| WO | 2013/116834 A2 | 8/2013 | |
| WO | 2014/074695 A1 | 5/2014 | |
| WO | 2015119642 A1 | 8/2015 | |
| WO | WO-2015138032 A2 * | 9/2015 | C12M 21/08 |

OTHER PUBLICATIONS

Wang et al. "Organization of Endothelial Cells, Pericytes, and Astrocytes into a 3D Microfluidic in Vitro Model of the Blood-Brain Barrier."Mol Pharm. Mar. 7, 2016;13(3):895-906. Epub Jan. 27, 2016 (Year: 2016).*
Prado-Lopez et al. "Hypoxia promotes efficient differentiation of human embryonic stem cells to functional endothelium."Stem Cells. Mar. 31, 2010;28(3):407-18. (Year: 2010).*
Kusuma, Sravanti. "Stem Cell and Hypoxia-Based Approaches to Engineering Blood Vessels." 2014. The Johns Hopkins University, PhD dissertation (Year: 2014).*
Lippmann et al. "A retinoic acid-enhanced, multicellular human blood-brain barrier model derived from stem cell sources."Scientific Reports vol. 4, Article No. 4160 (2014) (Year: 2014).*
Ding et al. "Continuous hypoxia regulates the osteogenic potential of mesenchymal stem cells in a time-dependent manner." Molecular Medicine Reports 10(4) Aug. 2014 (Year: 2014).*
Baldea et al. "Effects of different hypoxia degrees on endothelial cell cultures—Time course study"Mech Ageing Dev.Jun. 2018;172:45-50. (Year: 2018).*
Oh et al. "The timing and duration of hypoxia determine gene expression patterns in cultured human trophoblasts."Placenta.Dec. 2011;32(12):1004-9. (Year: 2011).*
Amit et al. "Clonally derived human embryonic stem cell lines maintain pluripotency and proliferative potential for prolonged periods of culture."Dev Biol. Nov. 15, 2000;227(2):271-8. (Year: 2000).*
Lotz et al. "Sustained Levels of FGF2 Maintain Undifferentiated Stem Cell Cultures with Biweekly Feeding."PLoS One. 2013;8(2):e56289. (Year: 2013).*

(Continued)

*Primary Examiner* — Titilayo Moloye
(74) *Attorney, Agent, or Firm* — Nixon Peabody LLP; David S. Resnick; Jeanne Jodoin

(57) ABSTRACT

The invention relates to a method of creating a human blood-brain barrier (BBB) model from the differentiation of human pluripotent stem cells (hPSCs), wherein the BBB exhibits sustained transendothelial electrical resistances (TEER) over 2000 $\Omega \cdot cm^2$ for at least 3 days after seeding.

30 Claims, 12 Drawing Sheets

(56) References Cited

OTHER PUBLICATIONS

Brown et al. "Recreating blood-brain barrier physiology and structure on chip: A novel neurovascular microfluidic bioreactor." Biomicrofluidics 9(5):1-15 (2015).

Eigenmann et al., "Comparative study of four immortalized human brain capillary endothelial cell lines, hCMEC/D3, hBMEC, TY10, and BB19, and optimization of culture conditions, for an in vitro blood-brain barrier model for drug permeability studies", Fluids Barriers CNS 10(1) 33 (2013).

Kusuma et al. "Low oxygen tension enhances endothelial fate of human pluripotent stem cells." Arteriosclerosis, Thrombosis, and Vascular Biology 34(4):913-920 (2014).

Lee et al., "Hypoxic priming of mESCs accelerates vascular-lineage differentiation through HIF1-mediated inverse regulation of Oct4 and VEGF", EMBO Mol Med 4(9) 924-38 (2012).

Lippmann et al., "A retinoic acid-enhanced, multicellular human blood-brain barrier model derived from stem cell sources", Sci Rep 4(4160) 2014.

Lippmann et al., "Human Blood-Brain Barrier Endothelial Cells Derived from Pluripotent Stem Cells", Nat Biotechnol 30(8) 783-91 (2012).

Prado-Lopez et al., "Hypoxia promotes efficient differentiation of human embryonic stem cells to functional endothelium", Stem Cells 28(3) 407-18 (2010).

Song et al., "Oxygen tension regulates the maturation of the blood-brain barrier", Biochem Biophys Res Commun 290(1) 325-31 (2002).

Zhao et al., "Low-oxygen pretreatment enhances endothelial cell growth and retention under shear stress", Tissue Engineering Part C: Methods 15(2) 135-146 (2008).

He et al. "Cell-Culture Models of the Blood-Brain Barrier." Stroke 45(8): 2514-2526 (2014).

Park et al. "Hypoxia-enhanced Blood-Brain Barrier Chip recapitulates human barrier function, drug penetration, and antibody shuttling properties." bioRxiv 482463: 1-43 (2018).

Stebbins et al. "Differentiation and characterization of human pluripotent stem cell-derived brain microvascular endothelial cells" Methods 101: 93-102 (2016).

\* cited by examiner

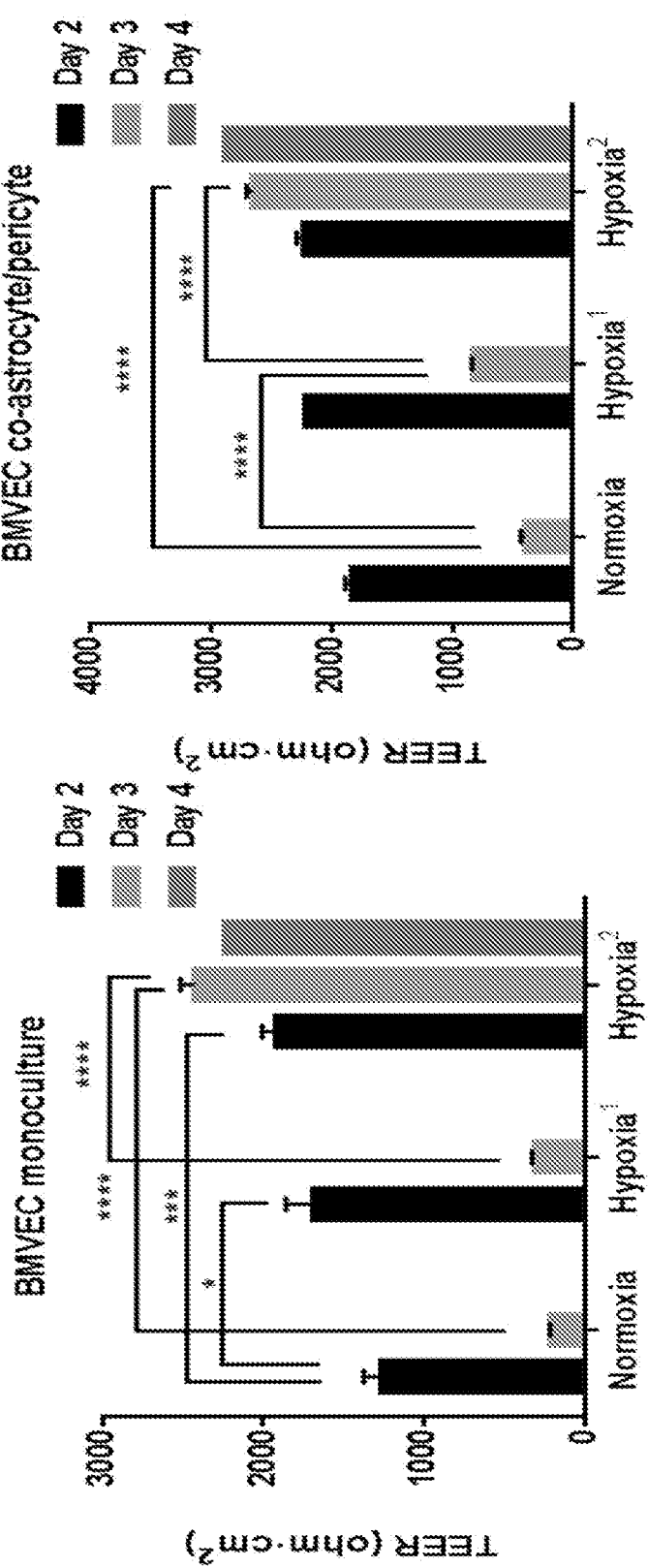

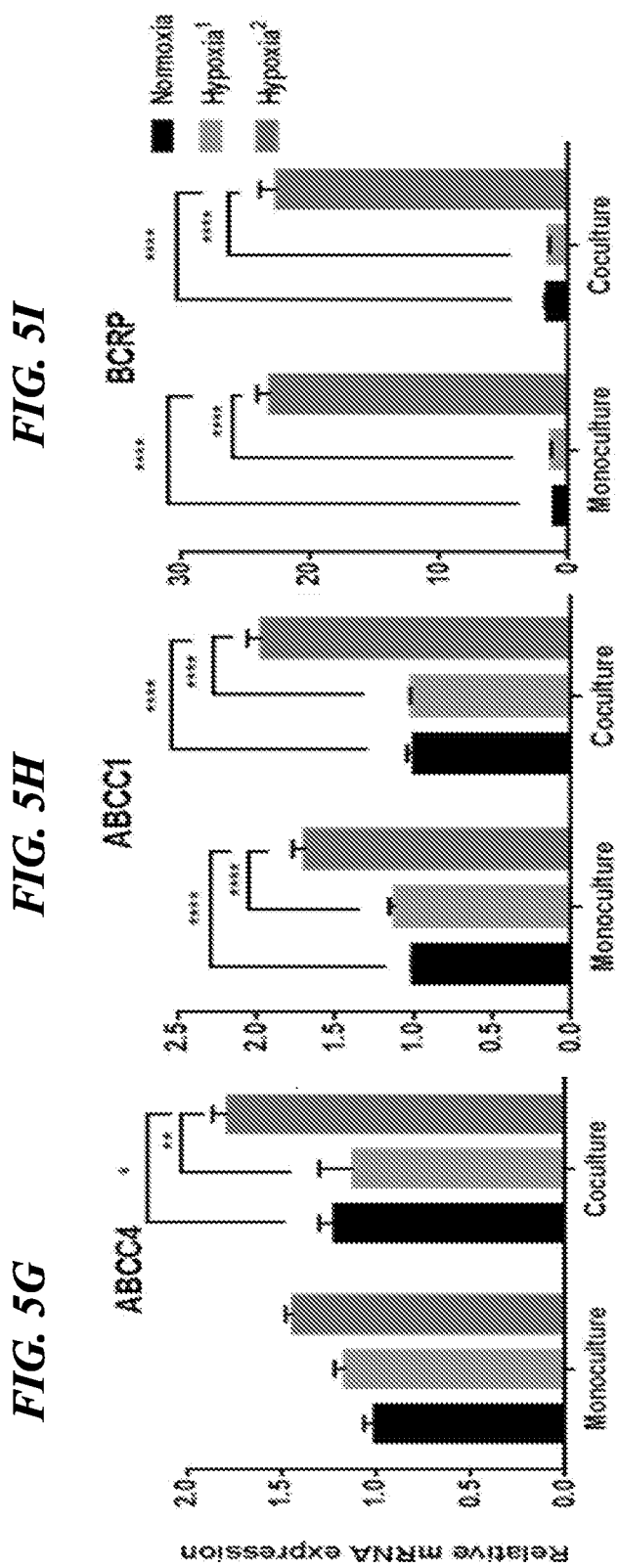

BLOOD-BRAIN BARRIER ENDOTHELIAL CELLS DERIVED FROM PLURIPOTENT STEM CELLS FOR BLOOD-BRAIN BARRIER MODELS

CROSS-REFERENCE TO RELATED APPLICATION

This application is a 35 U.S.C. § 371 National Phase Entry Application of International Application No. PCT/US2017/018150 filed Feb. 16, 2017, which designates the U.S. and claims benefit under 35 U.S.C. § 119(e) of U.S. Provisional Application No. 62/107,872, filed Feb. 16, 2016, the contents of which are incorporated herein by reference in their entireties.

GOVERNMENT SUPPORT

This invention was made with Government support under W911NF-12-2-0036 awarded by the U.S. Department of Defense (DARPA). The Government has certain rights in the invention.

FIELD OF THE INVENTION

The invention relates to methods of culturing and composition of brain microvascular endothelial cells (BMVECs), blood brain barrier models comprising the BMVECs and kits comprising the BMVECs.

BACKGROUND OF THE INVENTION

The blood-brain barrier (BBB) comprises the brain microvascular endothelial cells (BMVECs) which line brain capillaries and control trafficking between the bloodstream and neural tissue. These properties are tightly regulated by the surrounding microenvironment (termed the neurovascular unit) throughout BBB development and into adulthood. While this barrier is essential for preserving healthy brain activity, its dysfunction and deregulation is implicated in a number of neurological diseases. Moreover, an intact BBB serves as a major bottleneck for brain drug delivery. Unfortunately, studies involving BBB development and regulation can be difficult and time-consuming to conduct in vivo, and the ability to screen brain-penetrating therapeutics in vivo is restricted to a small number of researchers with technical expertise in such techniques. Thus, researchers often use more accessible platforms, i.e. in vitro BBB models, to study interactions between BMVECs and the neurovascular unit and to conduct compound library screens for prospective BBB-permeant drugs.

In the past, the cells for an in vitro BBB model comprised cultures of primary human isolated from autopsy tissue or from freshly resected brain specimens derived from tumor or epilepsy patients. These cells offer similarity to the phenotypic characteristics of the human brain endothelium, but they are extremely time consuming and expensive to generate. On the other hand, immortalized human brain capillary endothelial cell lines including hCMEC/D3, hBMVEC, TY10, and BB19 have been proposed as alternatives, but the immortalization process alters expression and interactions of numerous proteins as well as the physiological cell cycle. See Eigenmann et al., "Comparative study of four immortalized human brain capillary endothelial cell lines, hCMEC/D3, hBMVEC, TY10, and BB19, and optimization of culture conditions, for an in vitro blood-brain barrier model for drug permeability studies," Fluids Barriers CNS 10:33 (2013). Furthermore, both primary and immortalized human brain capillary endothelial cells have poor barrier properties, including low baseline transendothelial electrical resistance (TEER) and discontinuous tight junction and transporter protein expression/function.

To create a robust, scalable human BBB in vitro model, E. Shusta's team (University of Madison Wis.) used human pluripotent stem cells (PSCs) differentiation and generated pure endothelial cells having many BBB properties in concert with a neural cell co-differentiation providing important micro-environmental cues. See Lippmann et al., Human Blood-Brain Barrier Endothelial Cells Derived from Pluripotent Stem Cells, Nat. Biotechnol., 30:783 (2012). The cells, termed iPSC derived (or hPSC derived) brain microvascular endothelial cells ("BMVECs" or "BMVECs"), had well-organized tight junctions, appropriate expression of nutrient transporters and polarized efflux transporter activity, According to their reports, TEER value of monoculture BMVEC reached to 2000 $\Omega \cdot cm^2$, and in optimal co-culture condition (with rentinoic acid) reached to 3500 $\Omega \cdot cm^2$ within 24-48 h after seeding. However, the value decreased rapidly after the peak value at day 2. See Lippmann et al., "A retinoic acid-enhanced, multicellular human blood-brain barrier model derived from stem cell sources," Sci. Rep. 4:4160 (2014).

What is needed is an improved culture method for generating cells which better mimic the structure and function of the blood brain barrier.

SUMMARY OF THE INVENTION

The inventors have discovered that when pluripotent stem cells (PSCs) are exposed to hypoxic conditions for a period of time during their differentiation process into brain microvascular endothelial cells (BMVECs), the resultant BMVECs in culture form a BBB that have characteristics closer to a naturally occurring BBB. For example, the TEER of the hypoxia condition-derived BBB is high, over 2000 $\Omega \cdot cm^2$ and is well sustained for over three days in culture. The exposure to hypoxia is for about one to about ten days for low oxygen during their differentiation process. The low oxygen tension is about 5% $O_2$.

Accordingly, embodiments disclosed herein relates to improved methods of culturing and preparing better brain-like endothelial cells for various in vitro uses, such as building BBB models.

Additionally, embodiments disclosed herein relates to culturing brain cells (or their precursors) and particularly endothelial cells (or their precursors) in a fluidic device, such as a microfluidic device, under hypoxic (low oxygen) conditions whereby the cells differentiate and/or mature into cells that better mimic the structure and function of the blood brain barrier. Good viability and function allow for measurements of barrier integrity and physiology, whether by trans-epithelial electrical resistance (TEER), patch clamp or other testing measures.

Specifically, disclosed is a method of creating a human blood-brain barrier (BBB) model comprising brain microvascular endothelial cells (BMVECs), the cells are derived from the differentiation of human pluripotent stem cells (hPSCs), wherein the BBB exhibits high metabolic barrier function, has a sustained transendothelial electrical resistance (TEER) of over 2000 $\Omega \cdot cm^2$ lasting for at least 3 days in vitro after seeding. The BMVECs are differentiated under hypoxic conditions. Such models with sustained BBB integrity would allow scientists to experiment in areas such as the BBB development and regulation, and also to screen brain-penetrating therapeutics.

Specifically, disclosed is a compositions comprising hPSCs-derived microvascular endothelial cells (BMVECs) having high metabolic barrier function and sustained TEERs, and uses of the compositions of cells. The BMVECs are differentiated under hypoxic conditions.

In some aspects, the disclosure contemplates culturing brain cells (or their precursors) and particularly endothelial cells (or their precursors) under hypoxic (low oxygen) conditions whereby the cells differentiate and/or mature into cells that better mimic the structure, function and integrity of the naturally occurring blood brain barrier, e.g., sustained high TEER over time. The culturing of cells and differentiation can occur in a fluidic device, such as a microfluidic device, or on trans-well culture dishes. This differentiation/culture procedure that incorporates an hypoxic component results in well differentiated endothelial cells that have good viability, and have high and sustained metabolic barrier function. The resultant endothelial confluent cells allow for the measurements of barrier integrity and physiology, whether by TEER, patch clamp or other testing measures.

In one embodiment, the present invention contemplates a microfluidic device comprising a membrane, the membrane comprising BMVECs that were cultured and differentiated under low oxygen conditions. In one embodiment, the membrane comprises a top surface and a bottom surface, the bottom surface comprising the BMVECs In one embodiment, the present invention contemplates a microfluidic device comprising a monoculture of BMVECs displaying TEER values of greater than 2000 $\Omega \cdot cm^2$ for at least three days of culture. In one embodiment the BMVECs are iPSC-derived and differentiated under low oxygen levels (e.g. ~2% to ~10%, or ~2% to ~5%, or ~3% to ~7%).

In one embodiment, the present invention contemplates a microfluidic device comprising a co-culture of BMVECs and at least one additional neural cell (and preferably two, e.g., astrocytes and pericytes), the co-culture displaying TEER values of greater than 2000 $\Omega \cdot cm^2$ for at least three days of culture. In one embodiment, the TEER value is greater than 2500 $\Omega \cdot cm^2$ at day four of culture. In one embodiment, the BMVECs are iPSC-derived and were differentiated under low oxygen levels (e.g. ~2% to ~10%, or ~2% to ~5%, or ~3% to ~7%).).

In one embodiment, the present invention contemplates a method of culturing cells, comprising: a) providing a microfluidic device comprising a membrane, the membrane comprising a top surface and a bottom surface; b) seeding cells on either the top surface or the bottom surface of the membrane; and c) culturing the seeded cells under low oxygen conditions (e.g. ~2% to ~10%, or ~2% to ~5%, or ~3% to ~7%) that support the maturation of BMVECs. In one embodiment, the cells are selected from the group consisting of stem cells, and cells differentiated from stem cells and primary cells. In one embodiment, the cells differentiated from stem cells are BMVECs. In one embodiment, the method further comprises seeding cells on the top surface and culturing the top surface seeded cells under conditions that support the maturation of at least one of astrocytes and neurons. In one embodiment, the BMVECs are GLUT-1+. In one embodiment, the low oxygen conditions comprise less than 10% oxygen. In one embodiment, the low oxygen conditions comprise approximately 5% oxygen. In one embodiment, the exposing to low oxygen conditions of step c) is for approximately twenty-four hours, after which the oxygen levels are increased.

In one embodiment, the present invention contemplates seeding cells on a microfluidic device and culturing the cells under low oxygen conditions (e.g. ~2% to ~10%, or ~2% to ~5%, or ~3% to ~7%). For example, in one embodiment, the present invention contemplates a method of generating brain microvascular endothelial cells, comprising the steps of: a) growing human stem cells on a surface; b) inducing differentiation of the cells by culturing the cells in unconditioned medium wherein endothelial cell (EC) regions of the cultures are observed; c) expanding the EC regions by culturing the cells in EC medium, the EC medium comprising retinoic acid (RA), so as to produce BMVECs; d) seeding the BMVECs on a microfluidic device having flow; and e) exposing the seeded cells to low oxygen conditions (e.g. ~2% to ~10%, or ~2% to ~5%, or ~3% to ~7%).

In one embodiment, the seeding is done on transwells (static culture) or standard culture (plates, flasks etc.) instead of a microfluidic device having flow. In one embodiment, the seeding is done on a membrane in a microfluidic device, the membrane positioned in the device to encounter the flow of culture media, the flow causing the cells seeded on the membrane to experience shear forces. In one embodiment, the BMVECs on the microfluidic device are GLUT-1+. In one embodiment, the low oxygen conditions comprise less than 10% oxygen. In one embodiment, the low oxygen conditions comprise approximately 5% oxygen. In one embodiment, the exposing to low oxygen conditions of step e) is for approximately twenty-four hours, after which the oxygen levels are increased. In one embodiment, the surface comprises extracellular matrix proteins. In one embodiment, the method further comprises the step off) growing the cells to confluence. In one embodiment, the human stem cells are hPSCs. In another embodiment, the human stem cells are induced pluripotent stem cells (iPSCs). In one embodiment, the method further comprises g) co-culturing the BMVECs with a cell type selected from the group consisting of astrocytes, pericytes and differentiated neural progenitor cells (NPCs), so as to create a BBB model in vitro.

In one embodiment, the present invention contemplates a method of producing BMVECs, comprising the steps of: a) growing human stem cells on a surface; b) inducing differentiation of the cells by culturing the cells in unconditioned medium wherein endothelial cell (EC) regions of the cultures are observed; c) exposing the cells to low oxygen conditions, and d) expanding the EC regions under the low oxygen conditions by culturing the cells in EC medium so as to produce brain microvascular endothelial cells (BMVECs). In one embodiment, the BMVECs are GLUT-$1^+$. In one embodiment, the low oxygen conditions comprise less than 10% oxygen. In one embodiment, the low oxygen conditions comprise approximately 5% oxygen. In one embodiment, the method further comprises e) seeding the BMVECs on transwells (or some other static culture device) or on a microfluidic device having flow. In one embodiment, the seeding is done on a membrane in a microfluidic device, the membrane positioned in the device to encounter the flow of culture media, the flow causing the cells seeded on the membrane to experience shear forces. In one embodiment, the method further comprises f) exposing the seeded cells to low oxygen conditions (~2% to ~10%, or ~2% to ~5%, or ~3% to ~7% oxygen). In one embodiment, the exposing to low oxygen conditions of step f) is for approximately twenty-four hours, after which the oxygen levels are increased (e,g, above 10% and more preferably to approximately 20%). In one embodiment, the surface comprises extracellular matrix proteins. In one embodiment, the method further comprises the step of g) growing the cells to confluence. In one embodiment, the human stem cells are human pluripotent stem cells (hPSCs). In one embodiment, the human stem cells are induced pluripotent stem cells (iPSCs).

In one embodiment, the present invention contemplates a method of generating BMVECs comprising the steps of: a) growing human stem cells on a surface; b) inducing differentiation of the cells by culturing the cells in unconditioned medium wherein endothelial cell (EC) regions of the cultures are observed; c) exposing the cells to low oxygen conditions, and d) expanding the EC regions under the low oxygen conditions by culturing the cells in EC medium, the EC medium comprising retinoic acid (RA), so as to produce BMVECs. In one embodiment, the BMVECs are GLUT-1+. In one embodiment, the low oxygen conditions comprise less than 10% oxygen.

In one embodiment, the low oxygen conditions comprise approximately 5% oxygen. In one embodiment, the method further comprises e) seeding the BMVECs on transwells (or some other static culture system) or on a microfluidic device having flow. In one embodiment, the seeding is done on a membrane in a microfluidic device, the membrane positioned in the device to encounter the flow of culture media, the flow causing the cells seeded on the membrane to experience shear forces. In one embodiment, the method further comprises f) exposing the seeded cells to low oxygen conditions (~2% to ~10%, or ~2% to ~5%, or ~3% to ~7% oxygen). In one embodiment, the exposing to low oxygen conditions of step f) is for approximately twenty-four hours, after which the oxygen levels are increased. In one embodiment, the surface comprises extracellular matrix proteins. In one embodiment, the method further comprises the step of g) growing the cells to confluence. In one embodiment, the human stem cells are human pluripotent stem cells (hPSCs). In one embodiment, aid human stem cells are induced pluripotent stem cells (iPSCs). In one embodiment, the method further comprises h) co-culturing the BMVECs with a cell type selected from the group consisting of astrocytes, pericytes and differentiated neural progenitor cells (NPCs), so as to create a BBB model in vitro.

In one embodiment, the present invention contemplates a method of generating BMVECs comprising the steps of: a) growing human stem cells on a surface; b) inducing differentiation of the cells by culturing the cells in unconditioned medium wherein endothelial cell (EC) regions of the cultures are observed; c) expanding the EC regions by culturing the cells in EC medium, the EC medium comprising retinoic acid (RA), so as to produce BMVECs; d) seeding the BMVECs on transwells or on a microfluidic device having flow; and e) exposing the seeded cells to low oxygen conditions. In one embodiment, the seeding is done on a membrane in a microfluidic device, the membrane positioned in the device to encounter the flow of culture media, the flow causing the cells seeded on the membrane to experience shear forces. In one embodiment, the BMVECs are GLUT-1+. In one embodiment, the low oxygen conditions comprise less than 10% oxygen. In one embodiment, the low oxygen conditions comprise approximately 5% oxygen. In one embodiment, the exposing to low oxygen conditions of step e) is for approximately twenty-four hours, after which the oxygen levels are increased (e.g., to 10% and more preferably 20% oxygen). In one embodiment, the surface comprises extracellular matrix proteins. In one embodiment, the method further comprises the step off) growing the cells to confluence. In one embodiment, the human stem cells are hPSCs. In one embodiment, the human stem cells are iPSCs. In one embodiment, the method further comprises g) co-culturing the BMVECs with a cell type selected from the group consisting of astrocytes, pericytes and differentiated NPCs, so as to create a BBB model in vitro.

Definitions

It is not intended that the present invention be limited by the nature of the "microfluidic device." However, preferred microfluidic devices are described in U.S. Pat. No. 8,647,861, hereby incorporated by reference, and they are microfluidic "organ-on-chip" devices comprising living cells in microchannels, e.g. cells on membranes in microchannels exposed to culture fluid at a flow rate. It is important to note that the features enabling the actuation of strain or mechanical forces on the cells within the "organ-on-chip" device are optional with regards to the "BBB-on-chip" and may be omitted. Flow is important and stands in contrast to static 2D culture. Using a flow in the microchannel(s) allows for the perfusion of cell culture medium throughout the cell culture during in vitro studies and as such offer a more in vivo-like physical environment. In simple terms, an inlet port allows injection of cell culture medium, blood, blood component or mixture thereof into a cell-laden microfluidic channel or chamber, thus delivering nutrients and oxygen to cells. An outlet port then permits the exit of remaining liquid as well as harmful metabolic by-products. While continuous flow is preferable due to its application of controlled shear forces, either of the device's fluidic paths could also be cultured under "stop flow" conditions, where the flow is engaged intermittently, interspersed by static culture.

Microfluidic devices are conveniently made of polydimethylsiloxane (PDMS), polyurethane, polycarbonate, polystyrene, polymethyl methacrylate, polyimide, styrene-ethylene-butylene-styrene (SEBS), polypropylene, or any combinations thereof. The present invention contemplates treatment of such substances to promote cell adhesion, selection or differentiation or fluid wetting such as treatments selected from the group consisting of plasma treatment, ion treatment, gas-phase deposition, liquid-phase deposition, adsorption, absorption or chemical reaction with one or more agents.

Additionally, the term "microfluidic" as used herein relates to components where moving fluid is constrained in or directed through one or more channels wherein one or more dimensions are 10 mm or smaller (microscale). Microfluidic channels may be larger than microscale in one or more directions, though the channel(s) may be on the microscale in at least one direction. In some instances the geometry of a microfluidic channel may be configured to control the fluid flow rate through the channel Microfluidic channels can be formed of various geometries to facilitate a wide range of flow rates through the channels. However, it is important to note that while the present disclosure makes frequent reference to "microfluidic" devices, much of what is taught applies similarly or equally to larger fluidic devices. Larger devices may be especially relevant if the "BBB-on-chip" is intended for therapeutic application. Examples of applications that may make advantage of larger fluidic devices include the use of the device for the generation of highly differentiated cells (e.g. the device can used to drive cells differentiation and/or maturation, whereupon the cells are extracted for downstream use, which may include implantation, use in an extracorporeal device, or research use), or use of the device for implantation or extracorporeal use, for example, as an artificial blood-brain barrier or a dialysis-like technology.

As used herein, the phrases "connected to," "coupled to," and "in communication with" refer to any form of interaction between two or more entities, including mechanical, electrical, magnetic, electromagnetic, fluidic, and thermal interaction. For example, in one embodiment, first and second channels in a microfluidic device are in fluidic communication with a fluid reservoir. Two components may be coupled to each other even though they are not in direct contact with each other. For example, two components may be coupled to each other through an intermediate component (e.g. tubing or other conduit).

The surfaces of the microchannels and/or the membrane can be coated with cell adhesive, selective or promotive molecules to support the attachment of cells and promote their organization into tissues. Where a membrane is used, tissues can form on either the upper surface of the membrane, the lower surface of the membrane, any of the surfaces of the channels or cavities present on either side of the membrane or any combination thereof. In one embodiment, different cells are living on the upper and lower surfaces, thereby creating one or more tissue-tissue interfaces separated by the membrane. The membrane may be porous, flexible, elastic, or a combination thereof with pores large enough to only permit exchange of gases and/or small chemicals, or large enough to permit migration and transchannel passage of large proteins, as well as whole living cells and/or portions thereof (e.g. the endfoot of an astrocyte). Depending on the size-scale of the pores and manufacturing preferences, the pores may be defined, for example, using lithography, molding, laser-drilling or track-etching, intrinsic to a selected material (for example, polyacrylamide gel, collagen gel, paper, cellulose) or engineered into the material (e.g. by generating an open-cell polymer or matrix).

There are many ways to evaluate the integrity and physiology of an in vitro system that mimics the blood brain barrier. Two of the most common methods are Transepithelial Electric Resistance (TEER) and Lucifer Yellow (LY) rejection. Importantly, manipulations must be performed using aseptic techniques in order for the cells to remain in culture without contamination. TEER measures the resistance to pass current across one or more cell layers on a membrane. The measurement may be affected by the pore size and density of the membrane, but it aims to ascertain cell and/or tissue properties. The TEER value is considered a good measure of the integrity of the cell monolayer.

Lucifer Yellow (LY) travels across cell monolayers only through passive paracellular diffusion (through spaces between cells) and has low permeability. Therefore it is considerably impeded in passing across cell monolayers with tight junctions. Permeability (Papp) for LY of ≤5 to 12 nm/s has been reported to be indicative of well-established monolayers.

BRIEF DESCRIPTION OF THE DRAWINGS

FIG. 4A is a bar graph showing TEER values of monoculture of iPSC-derived BMVECs differentiated under different oxygen levels, normoxia, hypoxia 1, and hypoxia 2 conditions. Data were analyzed with two-way analysis of variance (ANOVA) with Tukey test; *$P<0.05$, $P<0.01$, *$P<0.001$, ****$P<0.0001$.

FIG. 4B is a bar graph showing TEER values of iPSC-derived BMVEC differentiated under different oxygen levels, normoxia, hypoxia 1, and hypoxia 2 conditions. They were co-cultured with astrocytes and pericytes from D0. Data were analyzed with two-way analysis of variance (ANOVA) with Tukey test; *$P<0.05$, $P<0.01$, *$P<0.001$, ****$P<0.0001$.

FIG. 5A-5I show bar graphs of representative blood-brain barrier (BBB) transcript expression levels, as measured by RT-PCR quantification, in iPSC-derived BMVEC monoculture or co-culture with primary human astrocytes and pericytes. Transcripts were confirmed for (FIG. 5A) PCDH12 (Protocadherin 12), (FIG. 5B) GLUT1 (Glucose transporter 1), (FIG. 5C) ABCB1 (ATP binding cassette subfamily B) member 1, (FIG. 5D) INSR, (FIG. 5E) CAV1, (FIG. 5F) CLTC (Clathrin heavy chain), (FIG. 5G) ABCC4 (ATP binding cassette subfamily C member 4), (FIG. 5H) ABCC1 (ATP binding cassette subfamily C member 1), and (FIG. 5I) BCRP (Breast cancer resistance protein). The mRNA data for each transcripts are normalized with GAPDH (glyceraldehyde-3-phosphate dehydrogenase) mRNA expression. Data were analyzed with the multiple t-test.

FIG. 8A shows the bar graphs of the proteomics analysis of efflux pump proteins related proteins.

FIG. 8B shows the bar graphs of the proteomics analysis of proteins related to the formation of tight junctions.

DETAILED DESCRIPTION OF THE INVENTION

Figure 1:
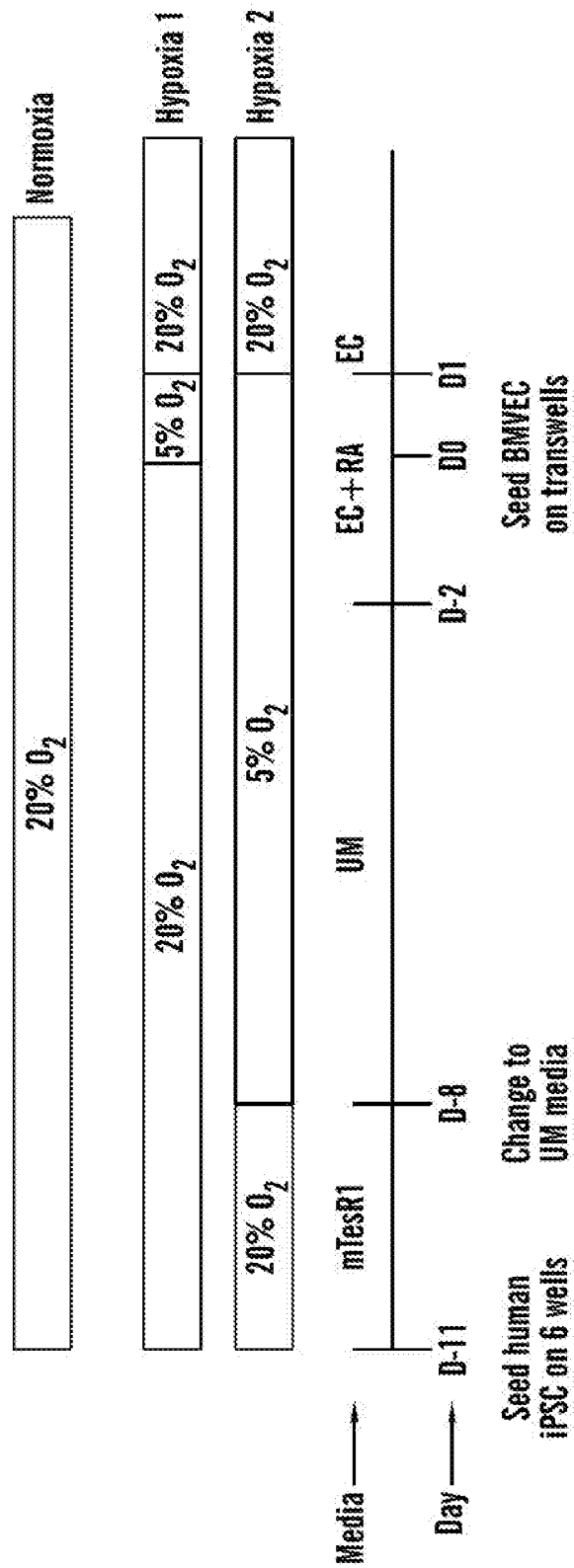
FIG. 1 shows two schemes, Hypoxia 1 and Hypoxia 2, for utilizing low oxygen conditions in connection with the differentiation and/or maturation of brain microvascular endothelial cells (BMVECs), including cell seeding (e.g. on a microfluidic device) followed by culture under low oxygen conditions. The alphabet "D" represents day' and the number following "D" indicates the specified number of days before Day zero (D0) as indicated with a minus sign, or the specified number of days after D0, e.g., D1=one day after D0. The control normal oxygen condition, also known as normoxia, is also shown.

Unless otherwise explained, all technical and scientific terms used herein have the same meaning as commonly understood by one of ordinary skill in the art to which this disclosure belongs. Definitions of common terms in molecular biology may be found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). Further, unless otherwise required by context, singular terms shall include pluralities and plural terms shall include the singular.

Unless otherwise stated, the present invention was performed using standard procedures known to one skilled in the art, for example, in Michael R. Green and Joseph Sambrook, Molecular Cloning: A Laboratory Manual, Cold Spring Harbor Laboratory Press, Cold Spring Harbor, N.Y., USA (2012); Sambrook et al., Molecular Cloning: A Laboratory Manual (4th ed.); Davis et al., Basic Methods in Molecular Biology, Elsevier Science Publishing, Inc., New York, USA (1986); Current Protocols in Molecular Biology (CPMB) (Fred M. Ausubel, et al. ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998), Methods in Molecular biology, Vol. 180, Transgenesis Techniques by Alan R. Clark editor, second edition, 2002, Humana Press, and Methods in Meolcular Biology, Vo. 203, 2003, Transgenic Mouse, edited by Marten H. Hofker and Jan van Deursen, which are all herein incorporated by reference in their entireties.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages will mean ±1%.

All patents and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present invention relates to methods and compositions comprising brain microvascular endothelial cells (BMVECs) that are differentiated from pluripotent stem cells (PSCs) in culture conditions of low oxygen tension.

Embodiments of the present invention are based, in part, on the discovery that brain microvascular endothelial cells (BMVECs) differentiated from pluripotent stem cells (PSCs) in the presence of low oxygen tension gave a better BBB structure and integrity, as determined by the sustained high TEER of the barrier exhibited over several days in culture in vitro.

The blood brain barrier (BBB) is a highly evolved microvasculature system composed of different specialized cell types including BMVECs lining the lumen brain vasculature, pericytes embedded within the abluminal basement membrane, and astrocytes with their endfeet directly contacting the other cell types. These three cell types together with the neurons, form what is termed the neurovascular unit (NVU). It is established that one of the important determinants of BMVECs differentiation and functionality is this multicellular local environment within the BBB and particularly the direct interaction with surrounding cells and the extracellular matrix. One important function of the BBB is to regulate exchange of substances between the blood and brain, and this is controlled by two very different mechanisms. First, the tight junctions between adjacent BECs form the basic structure to limiting paracellular permeability and secondly, transporters and receptors at the lumen and abluminal side of the BECs regulate transcellular transport.

The BBB is of major clinical relevance. Not only because dysfunction of the BBB leads to degeneration of the neurovascular unit, but also because drugs that are supposed to treat neurological disorders often fail to permeate the BBB. Because of its importance in disease and medical treatment, it would be highly advantageous to have a predictive model of the human blood-brain barrier.

Without limiting the invention in any manner to any particular mechanism, it is believed that, in human development, low oxygen environment drives blood vessel growth (angiogenesis) in the embryo by an increase of vascular endothelial growth factor (VEGF) levels. The subsequent re-oxygenization improves the maturation of brain endothelial cells (ECs). Indeed, previous studies have revealed that $O_2$ availability plays a role in EC differentiation for certain stem cell sources. Prado-Lopez et al., Hypoxia promotes efficient differentiation of human embryonic stem cells to functional endothelium," *Stem Cells*, 28(3): 407-18 (2010); Lee et al., "Hypoxic priming of mESCs accelerates vascular-lineage differentiation through HIF1-mediated inverse regulation of Oct4 and VEGF," *EMBO Mol Med.* 4(9):924-38 (2012); Kusuma et al., "Low oxygen tension enhances endothelial fate of human pluripotent stem cells," *Arterioscler Thromb Vasc Biol.* 34(4):913-202

(2014). However specific BMVEC differentiation from stem cells stimulated by oxygen tension has not been demonstrated.

In this regard, the inventors controlled the oxygen level during iPSC differentiation as per physiologically relevant oxygen tension during development and maturation of BMVEC in order to improve BBB attributes of iPSC-derived BMVEC. The inventors explored iPSC differentiation conditions of low oxygen to generate the BMVEC having stable barrier function.

The inventors have discovered that when PSCS are exposed to hypoxic conditions for a period of time during their differentiation process to brain microvascular endothelial cells (BMVECs), the resultant BMVECs in culture form a BBB that have characteristics closer to a naturally occurring BBB. For example, the TEER of the hypoxia condition-derived BBB high, over 2000 $\Omega \cdot cm^2$ and this sustained high TEER of the barrier is well sustained for over three days in culture. The exposure to hypoxia is for about one to about ten days for low oxygen during their differentiation process. The low oxygen tension is about 5% $O_2$.

Accordingly, in one aspect, provided herein is a method of producing BMVECs from human stem cells or PSCs wherein the BMVECs exhibit improved BBB characteristics in culture such as sustained high TEER of the barrier. The method comprising providing a population of PSCs, inducing differentiation of the PSCs to BMVECs under conditions of low oxygen tension for a period of time, and returning the differentiated BMVECs to normal oxygen tension (normoxia). The method is an in vitro culture method.

In one aspect, disclosed herein is a method for producing human brain-like endothelial cells (also known as BMVECs for this disclosure) comprising a) contacting a population of human stem cells or PSCs with a medium to support differentiation of the PSCs to BMVECs, b) exposing the PSCs to conditions of low oxygen tension for a period of time to obtain the BMVECs, and c) returning the cells to normal oxygen tension. In one embodiment, the method further comprises exposing PSCs to retinoic acid (RA) again under conditions of low oxygen tension for a period of time during the differentiation period before returning the cells to normoxia.

In one aspect, disclosed herein is a method for making BMVECs from PSCs comprising exposing a population of PSCs to conditions of low oxygen tension for a period of time and in a medium that support differentiation of the PSCs to BMVECs, and returning the cells to normal oxygen tension.

In one aspect, provided herein is a method of producing BMVECs from human stem cells or PSCs wherein the BMVECs exhibit improved BBB characteristics in culture such as sustained high TEER of the barrier, the method comprises providing a) a population of human stem cells or PSCs, b) contacting the population of human stem cells or PSCs with a medium to support differentiation of the PSCs to BMVECs under conditions of low oxygen tension for a period of time, c) contacting the cells of step b to a medium comprising RA under conditions of low oxygen tension for a period of time, and d) returning the cells to normal oxygen tension.

In one aspect, provided herein is a method of BMVECs culturing cells, comprising: a) providing a microfluidic device comprising a membrane, the membrane comprising a top surface and a bottom surface; b) seeding BMVECs cells on the bottom surface; and c) culturing the seeded BMVECs cells under low oxygen conditions that support the maturation of BMVECs. In one embodiment, the BMVECs are BMVECs produced by any one method described herein. In one embodiment, the membrane of the microfluidic device is also seeded with pericytes or astrocytes or both pericytes and astrocytes. In one embodiment, the pericytes or astrocytes are seeded on the top surface of the membrane. In one embodiment, the pericytes or astrocytes are seeded on the membrane before the BMVECs.

In one aspect, provided herein is a method of generating BMVECs, comprising the steps of: a) growing human stem cells or PSCs on a surface or solid support; b) inducing differentiation of the cells by culturing the cells in an unconditioned medium under conditions of low oxygen tension for a period of time; and c) continuing differentiation of the cells by culturing the cells in medium comprising retinoic acid (RA) again under conditions of low oxygen, so as to produce BMVECs. In one embodiment, the method further comprises d) seeding the BMVECs in a transwell or a microfluidic device having flow; and e) exposing the seeded cells to low oxygen conditions. In one embodiment, the unconditioned medium supports support differentiation of the PSCs to BMVECs.

In one aspect, provided herein is a method of producing BMVECs, comprising the steps of: a) growing human stem cells or PSCs on a surface or solid support; b) inducing differentiation of the cells by culturing the cells in unconditioned medium that supports support differentiation of the PSCs to BMVECs; and c) exposing the cells to low oxygen conditions for a period of time during the differentiation process so as to produce BMVECs. In one embodiment, during the differentiation process under low oxygen condition, the cells are exposed to RA. In one embodiment, during the differentiation process under low oxygen condition, the cells are exposed to RA for a period of about 2 days.

In one aspect, provided herein is a method of generating BMVECs, comprising the steps of: a) growing human stem cells or PSCs on a surface or solid support; b) inducing differentiation of the cells by culturing the cells in unconditioned medium; c) exposing the cells to low oxygen conditions, and d) expanding the cells under the low oxygen conditions by culturing the cells in EC medium, the EC medium comprising RA, so as to produce BMVECs.

In one aspect, provided herein is a method of generating BMVECs, comprising the steps of: a) growing human stem cells or PSCs on a surface or solid support; b) inducing differentiation of the cells by culturing the cells in unconditioned medium under conditions of low oxygen tension; c) expanding the cells by culturing the cells in EC medium, the EC medium comprising retinoic acid (RA) under conditions of low oxygen tension, so as to produce brain microvascular endothelial cells (BMVECs). In one embodiment, the method further comprises d) seeding the BMVECs in a transwell or a microfluidic device having flow; and e) exposing the seeded cells low oxygen conditions.

In one aspect, provided herein is a population of BMVECs generated by any of the method described herein.

In one aspect, provided herein is a composition comprising a population of BMVECs generated by any of the method described herein.

The BMVECs thus produced by the method described herein are then placed in TRANSWELLS and in microfluidic chips to assemble BBB models that are known in the art. See U.S. Pat. Nos. 5,260,210 and 7,060,428 U.S. Patent Application Publication Nos: US/2012/0015395, US2016/0040125, and International Patent Application Publications WO/2006/056879, WO/2007/072953 WO/2007/140340, WO2010014622 (PCT/US2009/051978), and WO2011159572 (PCT/US2011/039998), the contents of each are incorporated herein by reference in their entirety.

In one aspect, provided herein is a method of creating a blood-brain barrier (BBB) model, comprising the steps of: a) providing a population of BMVECs that are cultured differentiated under low oxygen conditions described herein, wherein the BMVECs are from the differentiation of pluripotent stem cells (PSCs); b) providing a mixture of neural cells such as astrocytes, pericytes, and neural progenitor cells; c) co-culturing the BMVECs with a cell type selected from the group consisting of pericytes, astrocytes and differentiated neural progenitor cells (NPCs) to confluence, wherein a blood brain barrier model is created.

In one aspect, provided herein is a method of creating an improved mammalian blood-brain barrier (BBB) model that has TEER values of greater than 2000 $\Omega \cdot cm^2$ for at least three days of culture, comprising the steps of: a) providing a population of BMVECs that are cultured differentiated under low oxygen conditions described herein, wherein the BMVECs are from the differentiation of pluripotent stem cells (PSCs); b) providing a mixture of neural cells such as astrocytes, pericytes, and neural progenitor cells; c) co-culturing the BMVECs with a cell type selected from the group consisting of pericytes, astrocytes and differentiated neural progenitor cells (NPCs) to confluence, wherein a blood brain barrier model is created.

In one aspect, provided herein is a method of creating an improved mammalian blood-brain barrier (BBB) model that has TEER values of greater than 2000 $\Omega \cdot cm^2$ for at least three days of culture, comprising the steps of: a) providing a population of BMVECs that are cultured differentiated under low oxygen conditions described herein, wherein the BMVECs are from the differentiation of a population of human stem cell or pluripotent stem cells (PSCs) by (i) contacting the population of human stem cells or PSCs with a medium to support differentiation of the PSCs to BMVECs, (ii) exposing the cells to conditions of low oxygen tension for a period of time, (iii) contacting the cells of step b to a medium comprising RA under continued conditions of low oxygen tension for a period of time, and (iv) returning the cells to normal oxygen tension; b) providing a mixture of neural cells such as astrocytes, pericytes, and neural progenitor cells; c) co-culturing the BMVECs with a cell type selected from the group consisting of pericytes, astrocytes and differentiated neural progenitor cells (NPCs) to confluence, wherein a blood brain barrier model is created.

In one aspect, provided herein is a mammalian blood-brain barrier (BBB) model created by the method of creating an improved mammalian blood-brain barrier (BBB) model that has TEER values of greater than 2000 $\Omega \cdot cm^2$ for at least three days of culture, the method comprising the steps of: a) providing a population of BMVECs that are cultured differentiated under low oxygen conditions described herein, wherein the BMVECs are from the differentiation of pluripotent stem cells (PSCs); b) providing a mixture of neural cells such as astrocytes, pericytes, and neural progenitor cells; c) co-culturing the BMVECs with a cell type selected from the group consisting of pericytes, astrocytes and differentiated neural progenitor cells (NPCs) to confluence, wherein a blood brain barrier model is created.

In one aspect, provided herein is an apparatus comprising a membrane, the membrane comprising BMVECs that are cultured differentiated under low oxygen conditions described herein. In one embodiment, the BMVECs are seeded on the bottom surface of the membrane in the apparatus. In one embodiment, the apparatus further comprises pericytes or astrocytes. In one embodiment, the pericytes or astrocytes or both cell types are seeded on the top surface of the membrane. In one embodiment, the pericytes or astrocytes are seeded on the membrane before the BMVECs. In one embodiment, the BMVECs are grown to confluence on the membrane. In one embodiment, the pericytes or astrocytes are grown to confluence on the membrane.

In one aspect, provided herein is an apparatus comprising a monoculture of BMVECs are cultured differentiated under low oxygen conditions described herein and the cells displaying TEER values of greater than 2000 $\Omega \cdot cm^2$ for at least three days of culture. In one embodiment, the BMVECs are grown to confluence in the apparatus.

In one aspect, provided herein is an apparatus having a membrane comprising a co-culture of BMVECs and astrocytes and pericytes, the co-culture displaying TEER values of greater than 2000 $\Omega \cdot cm^2$ for at least three days of culture. In one embodiment, the BMVECs are cultured differentiated under low oxygen conditions described herein. In one embodiment, the BMVECs are seeded on the bottom surface of the membrane in the apparatus. In one embodiment, the apparatus further comprises pericytes or astrocytes. In one embodiment, the pericytes or astrocytes or both cell types are seeded on the top surface of the membrane. In one embodiment, the pericytes or astrocytes are seeded on the membrane before the BMVECs. In one embodiment, the BMVECs are grown to confluence on the membrane. In one embodiment, the pericytes or astrocytes are grown to confluence on the membrane.

In one aspect, provided herein is a microfluidic device comprising a membrane, the membrane comprising BMVECs that are cultured differentiated under low oxygen conditions described herein. In one embodiment, the BMVECs are seeded on the bottom surface of the membrane in the microfluidic device. In one embodiment, the microfluidic device further comprises pericytes or astrocytes. In one embodiment, the pericytes or astrocytes or both cell types are seeded on the top surface of the membrane. In one embodiment, the pericytes or astrocytes are seeded on the membrane before the BMVECs. In one embodiment, the BMVECs are grown to confluence on the membrane. In one embodiment, the pericytes or astrocytes are grown to confluence on the membrane.

In one aspect, provided herein is a microfluidic device comprising a monoculture of BMVECs are cultured differentiated under low oxygen conditions described herein and the cells displaying TEER values of greater than 2000 $\Omega \cdot cm^2$ for at least three days of culture. In one embodiment, the BMVECs are grown to confluence on the device.

In one aspect, provided herein is a microfluidic device having a membrane comprising a co-culture of BMVECs and astrocytes and pericytes, the co-culture displaying TEER values of greater than 2000 $\Omega \cdot cm^2$ for at least three days of culture. In one embodiment, the BMVECs are cultured differentiated under low oxygen conditions described herein. In one embodiment, the BMVECs are seeded on the bottom surface of the membrane in the microfluidic device. In one embodiment, the microfluidic device further comprises pericytes or astrocytes. In one embodiment, the pericytes or astrocytes or both cell types are seeded on the top surface of the membrane. In one embodiment, the pericytes or astrocytes are seeded on the membrane before the BMVECs. In one embodiment, the BMVECs are grown to confluence on the membrane. In one embodiment, the pericytes or astrocytes are grown to confluence on the membrane.

In one aspect, provided herein is a transwell comprising a membrane, separating the transwell into two compartments, an apical (top) chamber and a basal (bottom) chamber, the transwell comprising BMVECs that are cultured differentiated under low oxygen conditions described herein. In one embodiment, the BMVECs are seeded on the apical chamber in the transwell. In one embodiment, the transwell further comprises pericytes or astrocytes or both cell types. In one embodiment, the pericytes or astrocytes or both cell types are seeded on the basal chamber of the transwell. In one embodiment, the pericytes or astrocytes or both cell types are seeded on the transwell before the BMVECs. In one embodiment, the BMVECs are grown to confluence on the membrane. In one embodiment, the pericytes or astrocytes are grown to confluence on the membrane.

In one aspect, provided herein is a transwell having a membrane, the transwell comprising a monoculture of BMVECs are cultured differentiated under low oxygen conditions described herein and the cells displaying TEER values of greater than 2000 $\Omega \cdot cm^2$ for at least three days of culture. In one embodiment, the membrane separates the transwell into two compartments, an apical (top) chamber and a basal (bottom) chamber. In one embodiment, the BMVECs are seeded on the apical chamber in the transwell. In one embodiment, the BMVECs are grown to confluence on the membrane.

In one aspect, provided herein is a transwell having a membrane comprising a co-culture of BMVECs and (i) astrocytes; or (ii) pericytes; or (iii) both astrocytes and pericytes, the co-culture displaying TEER values of greater than 2000 $\Omega \cdot cm^2$ for at least three days of culture. In one embodiment, the BMVECs are cultured differentiated under low oxygen conditions described herein. In one embodiment, the BMVECs are seeded on the apical chamber in the transwell. In one embodiment, the transwell further comprises pericytes or astrocytes or both cell types. In one embodiment, the pericytes or astrocytes or both cell types are seeded on the basal chamber of the transwell. In one embodiment, the pericytes or astrocytes or both cell types are seeded on the transwell before the BMVECs. In one embodiment, the BMVECs are grown to confluence on the membrane. In one embodiment, the pericytes or astrocytes are grown to confluence on the membrane.

In one aspect, provided herein is an in vitro BBB model comprising a microfluidic device comprising a membrane, the membrane comprising BMVECs that are cultured differentiated under low oxygen conditions described herein. In one embodiment, the BMVECs are seeded on the bottom surface of the membrane in the microfluidic device. In one embodiment, the microfluidic device further comprises pericytes or astrocytes. In one embodiment, the pericytes or astrocytes or both cell types are seeded on the top surface of the membrane. In one embodiment, the pericytes or astrocytes are seeded on the membrane before the BMVECs. In one embodiment, the BMVECs are grown to confluence on the membrane. In one embodiment, the pericytes or astrocytes are grown to confluence on the membrane.

In one aspect, provided herein is an in vitro BBB model comprising a microfluidic device comprising a monoculture of BMVECs are cultured differentiated under low oxygen conditions described herein and the cells displaying TEER values of greater than 2000 $\Omega \cdot cm^2$ for at least three days of culture. In one embodiment, the BMVECs are grown to confluence on the membrane.

In one aspect, provided herein is an in vitro BBB model comprising a microfluidic device having a membrane comprising a co-culture of BMVECs and astrocytes and pericytes, the co-culture displaying TEER values of greater than 2000 $\Omega \cdot cm^2$ for at least three days of culture. In one embodiment, the BMVECs are cultured differentiated under low oxygen conditions described herein. In one embodiment, the BMVECs are seeded on the bottom surface of the membrane in the microfluidic device. In one embodiment, the microfluidic device further comprises pericytes or astrocytes. In one embodiment, the pericytes or astrocytes or both cell types are seeded on the top surface of the membrane. In one embodiment, the pericytes or astrocytes are seeded on the membrane before the BMVECs. In one embodiment, the BMVECs are grown to confluence on the membrane. In one embodiment, the pericytes or astrocytes are grown to confluence on the membrane.

In one aspect, provided herein is an in vitro BBB model comprising a transwell comprising a membrane, separating the transwell into two compartments, an apical (top) chamber and a basal (bottom) chamber, the transwell comprising BMVECs that are cultured differentiated under low oxygen conditions described herein. In one embodiment, the BMVECs are seeded on the apical chamber in the transwell. In one embodiment, the transwell further comprises pericytes or astrocytes or both cell types. In one embodiment, the pericytes or astrocytes or both cell types are seeded on the basal chamber of the transwell. In one embodiment, the pericytes or astrocytes or both cell types are seeded on the transwell before the BMVECs. In one embodiment, the BMVECs are grown to confluence on the membrane. In one embodiment, the pericytes or astrocytes are grown to confluence on the membrane.

In one aspect, provided herein is an in vitro BBB model comprising a transwell having a membrane, the transwell comprising a monoculture of BMVECs are cultured differentiated under low oxygen conditions described herein and the cells displaying TEER values of greater than 2000 $\Omega \cdot cm^2$ for at least three days of culture. In one embodiment, the membrane separates the transwell into two compartments, an apical (top) chamber and a basal (bottom) chamber. In one embodiment, the BMVECs are seeded on the apical chamber in the transwell. In one embodiment, the BMVECs are grown to confluence on the membrane.

In one aspect, provided herein is an in vitro BBB model comprising a transwell having a membrane comprising a co-culture of BMVECs and (i) astrocytes; or (ii) pericytes; or (iii) both astrocytes and pericytes, the co-culture displaying TEER values of greater than 2000 $\Omega \cdot cm^2$ for at least three days of culture. In one embodiment, the BMVECs are cultured differentiated under low oxygen conditions described herein. In one embodiment, the BMVECs are seeded on the apical chamber in the transwell. In one embodiment, the transwell further comprises pericytes or astrocytes or both cell types. In one embodiment, the pericytes or astrocytes or both cell types are seeded on the basal chamber of the transwell. In one embodiment, the pericytes or astrocytes or both cell types are seeded on the transwell before the BMVECs. In one embodiment, the BMVECs are grown to confluence on the membrane. In one embodiment, the pericytes or astrocytes are grown to confluence on the membrane.

In one aspect, provided herein are BMVECs made according to methods described herein for use in medicine or for in vitro testing of new drugs. Testing can be performed in in vitro model of BBB such as a microfluidic chip that simulate a brain with intact BBB, or a transwell described herein.

In one aspect, provided herein is a use of BMVECs made according to methods described herein for use as an in vitro model of BBB.

In one aspect, provided herein is a method for evaluating blood-brain barrier permeability of a test substance, cell or protein comprising exposing the test substance, cell or protein to the BMVECs made according to methods described herein. The test substance may be any synthetic or natural compound, with variable molecular weight and hydrophilicity/hydrophobicity ratio. The method of the disclosure can measure passive diffusion or active transport, as appreciated by those skilled in the art. Efflux transport can be measured wherein measuring permeability values is performed in the presence or absence of inhibitors of the efflux pumps such as, but not limited to, cyclosporin-A, PSC-833, MK-571, KO-143. The methods of the present disclosure can also be used to measure blood brain barrier metabolism of a substance by measuring permeability values and profiling the metabolic degradation of compounds of interest as a function of time using quantitative analytical techniques such as high pressure liquid chromatography and mass spectrometry. Test substances that prove to pass our BBB in vitro model may be further analyzed for their pharmacological profile.

In one embodiment of any one aspect described herein, the test substance is any synthetic or natural compound or a drug.

In one embodiment of any one aspect described herein, wherein is measured efflux transport, preferably in the presence or absence of inhibitors of the efflux pumps.

In one embodiment of any one aspect described herein, efflux pumps are at least one of the following: cyclosporin-A, PSC-833, MK-571, KO-143, verapamil, elacridar.

In one embodiment of any one aspect described herein, the in vitro BBB model of the present disclosure can be useful as a method for determining the toxicity of a test substance or vector towards the BBB. In this case, the method comprises the culture of the brain endothelial-like cells in the presence of the test substance and assessing its viability after a certain time. A range of concentrations of the test substance can be used to determine the $IC_{50}$. Cell viability can be determined by a live/dead assay using calcein and propidium iodide as reagents, ATP production, cell membrane damage by the release of lactate dehydrogenase, cell replication by a BrdU assay.

In one aspect, provided herein is a method for evaluating the viability or metabolism of BBB after contact with a test substance, cell or protein which comprises the following steps: contacting a test substance, cell or protein to the BMVECs made according to methods described herein, and analyzing the viability or metabolism of the BMVECs.

In one aspect, provided herein is a method for evaluating the BBB after contact with a test substance, cell or protein which comprises the following steps: contacting a test substance, cell or protein to the BMVECs made according to methods described herein, and measuring the TEER of the BBB. A decrease in the TEERs in the presence of the test substance compared to in the absence of test substance indicate that the test substance is detrimental to the BBB.

In one aspect, provided herein is a kit for measuring blood-brain barrier permeability of a substance, comprising the in vitro BMVECs made according to methods described herein.

In one aspect, provided herein is a kit comprising the in vitro BMVECs made according to methods described herein and a transwell apparatus. The kit further comprises pericytes or astrocytes or both pericytes and astrocytes.

In one aspect, provided herein is a kit comprising a microfluidic device having the in vitro BMVECs made according to methods described herein. The kit further comprises pericytes or astrocytes or both pericytes and astrocytes.

In one aspect, provided herein is a kit comprising a microfluidic device, a transwell apparatus, in vitro BMVECs made according to methods described herein, both pericytes and astrocytes.

In one aspect, provided herein is a kit comprising in vitro BMVECs made according to methods described herein, both pericytes and astrocytes.

In one embodiment of any one aspect of a kit described, the kit further comprises instructions on the culturing and seeding of the BMVECs for use to produce a BBB model.

A non-limiting example of culturing PSCs and differentiating the PSCs to BMVECs under hypoxic conditions is as follows. Approximately 180,000 human pluripotent stem cells (hPSCs) were seeded on a 6-cm plastic culture dish in mTeSR media under 37° C., 5% $CO_2$, 20% $O_2$ culture condition. Normoxia is defined as 20% $O_2$ culture condition. The culture dish was coated with MATRIGEL™. The mTeSR medium was changed every day for 48-72 hours. When the cell density reaches to 250,000 per well, mTeSR medium was removed and replaced with conditioned UM medium prepared as following; in a 500 mL filter unit, combine 392.5 mL Dulbecco's modified eagle medium/F12 (DMEM/F12) (Invitrogen 11330-057) with 100 mL of KOSR, 5 mL of non-essential amino acids (Invitrogen 11140-050), 2.5 mL of Glutamax (Invitrogen 35050-061), and 3.5 μL of β-mercaptoethanol (Sigma M3148). The plates were placed under 37° C., 5% $CO_2$, 5% $O_2$ culture condition (hypoxic). The fresh unconditioned medium (UM) media was conditioned in hypoxic condition for 3 hours, and used to replace the media in the culture dish with the differentiating hPSCs under hypoxic conditions. The media in the culture dish is changed daily for 7 days. At day 7 after switching to UM media/hypoxic condition, the media is removed and replaced with hypoxic-conditioned endothelial cell (EC)+retinoic acid (RA) medium prepared as following; add 1 mL of platelet poor plasma-derived serum (PDS) (Fisher 50-443-029) to 100 mL of human endothelial serum-free medium (hESFM) (Invitrogen 11111-044) and bring to 20 ng/mL basic fibroblast growth factor (bFGF) (R&D Systems 233-FB). Filter sterilize before use and add 10 uM RA to EC medium just prior to feeding cells. Place the culture dish under hypoxic culture condition (37° C., 5% $CO_2$, 5% $O_2$) for two days.

A non-limiting example of assembling a BBB model in a transwell using the hypoxia differentiated PSCs-to-BMVECs is as follows. To assemble the BBB model on 0.33-cm polyester 0.4 μm pore sized transwell, the harvested primary human astrocytes and pericytes were seeded on the 24-well plate (basal chamber) with 0.035 million cells and 0.015 million cells per well, respectively, in EC+RA medium. The differentiated BMVECs on 6-cm plastic culture dish were dissociated using Accutase, harvested, and seeded on transwell (apical chamber) coated with collagen IV (400 ug/ml) and fibronectin (100 ug/ml) overnight with density of 1.65 million cells per well in EC+RA medium. The culture plates were incubated under hypoxic condition (37° C., 5% $CO_2$, 5% $O_2$), and after 24 hour, EC+RA media was switched to EC media prepared as following; add 1 mL of PDS (Fisher 50-443-029) to 100 mL of hESFM, and filter sterilized. The transepithelial electrical resistance (TEER) value was measured using an EVOM Volt/Ohm meter (World Precision Instruments, UK), equipped with a pair of chopstick electrodes. The culture plates were moved to normoxia incubation condition (37° C., 5% $CO_2$, 20% $O_2$). To maintain the culture, EC media was changed daily.

A non-limiting example of assembling a BBB model in a microfluidic chip having flow, using the hypoxia differentiated PSCs-to-BMVECs is as follows. To assemble the BBB model on microfluidic chips, polydimethylsiloxane (PDMS) microfluidic chip was plasma treated (0.5 mbar, 50 W, 2 min) and coated with 0.01% poly-L-lysine solution for 1 hour. Subsequently, 400 ug/ml collagen IV and 100 µg/ml fibronectin were treated to microfluidic chips and incubated overnight in normal cell culture condition (37 C, 5% $CO_2$, 20% $O_2$). A day after coating, ECM solution was rinsed with EC+RA medium. The harvested astrocytes and pericytes were resuspended at 0.7 and 0.3 million cells/mL in EC+RA medium. Mixture of cells was seeded on apical microchannel, and placed in incubator for 1 hour allowing the cells to adhere to membrane. The differentiated BMVECs on 6-cm plastic culture dish were dissociated using Accutase, harvested, and resuspended 25 million cells/mL in degassed EC+RA media. The differentiated BMVECs were seeded on basal micro-channel, and flip the entire PDMS chip upside down in petri dish to allow the BMVEC to attach to the membrane. At 5 hours after flipping the chips, flip back the chip and apply fresh EC+RA medium on the surface of the chips, and place it under hypoxic condition (37° C., 5% $CO_2$, 5% $O_2$). A day after seeding, EC+RA medium was switched to EC media, and chip was placed in normoxia condition (37° C., 5% $CO_2$, 20% $O_2$). To measure the TEER in BBB chip, chip-integrated electrode can be utilized as TEER sensor.

A non-limiting example of the isolation of pericytes for the co-cultures disclosed here is as follows. Pericytes may be extracted from freshly collected bovine brain capillaries. Brain capillaries were collected on a 60 µm nylon sieve (Blutex®, Saati, France) as described by Meresse et al. (1989) and suspended in Hanks Balanced Salt Solution (HBSS, Sigma-Aldrich) containing 10 mM HEPES and 0.1% BSA. This suspension was centrifuged at 1000 g for 7 min at room temperature. The pellet was then digested with 2 mg/mL collagenase-dispase (preferably Roche Diagnostics), 10 µg/mL DNaseI (Roche Diagnostics) and 0.147 µg/mL TLCK (Sigma-Aldrich), for 30 minutes at 37° C. in a shaking water bath. After washes, the digested capillaries were seeded onto growth factor reduced Matrigel (preferably BD Biosciences)-coated dishes (preferably Corning) containing pericyte growth culture medium: DMEM (Life Technologies) supplemented with 20% fetal calf serum (Integro), 2 mM L-glutamine (Merck Chemicals), 50 µg/mL gentamicin (Biochrom AG) and 1 ng/mL bFGF (Sigma-Aldrich). The medium was changed every other day. Pericytes and endothelial cells migrated from the vessels walls. Pericytes rapidly overgrew from capillaries and invaded the whole surface of the dishes. Confluent cultures consisting almost exclusively of pericytes, were dissociated using trypsin/EDTA saline solution (0.05%/0.02% Biochrom AG), and cells were frozen in liquid nitrogen. For experiments, each pericyte vial was rapidly thawed and seeded in gelatin (sigma-Aldrich)-coated 60-mm Petri dishes containing pericyte culture medium. After thawing, there were no endothelial cells left in cultures. Pericytes were subcultured at a split ratio 1/3, and were used at passages≤3.

A non-limiting example of co-culture experiments comprising BMVECs and pericytes is as follows. Astrocytes can also be added. Pericytes can be initially seeded on 60-mm gelatin-coated petri dishes and cultured in Dulbecco's Modified Eagle's Medium (DMEM) (Life Technologies) supplemented with 20% (v/v) fetal bovine serum (FBS) (Life Technologies), 2 mM L-glutamine, 50 µg/mL gentamycin and 1 ng/mL basic fibroblast growth factor (bFGF). The cells reached confluency after 2 days. $45 \times 10^3$ cells were seeded into each well of 12-well plates (Costar). BMVECs growing on gelatin-coated 100 mm petri dishes in EGM-2 (with all the supplements except FBS and gentamycin/amphotericin) supplemented with 2% (v/v) FBS, 50 µg/mL gentamycin (Biochrom AG) and 1 ng/mL home-made bFGF were trypsinized and cells were seeded at a density of $8 \times 10^4$/insert onto the MATRIGEL-coated (BD Biosciences) Transwell® inserts (preferably Costar). After 6 days in co-culture, the experiments were carried out.

In one embodiment of any one aspect described herein, the method comprises plating or seeding the PSCs on a solid support or surface such as a membrane or the surface of a tissue culture petri dish. The plated or seeded PSCs are then allowed to adhere to the solid support.

In one embodiment of any one aspect described herein, the solid support on which PSCs are cultured and differentiated, or differentiated BMVECs are grown to confluence to form the in vitro BBB model is a support or surface from which one can determine the presence or absence of tight junctions between BMVECs, such as by direct or indirect visualization or by determining the permeability of the in vitro BBB to molecules that would normally pass or not pass through the tight junctions of the BBB. Exemplary solid supports or surfaces include petri plates, wells of microtiter plates, slides, and filters (e.g., nitrocellulose, nylon membranes, etc, suitable for confluent growth of endothelial cells).

In one embodiment of any one aspect described herein, the solid support is a semi-permeable filters or membranes. Non-limiting examples include Nucleopore polycarbonate filters (Costar, Inc., Cambridge, Mass.), Millicell CM and HA porous nitrocellulose filters (Millipore Corp, Bedford, Mass.), and collagen membranes.

In one embodiment of any one aspect described herein, the solid support is a plastic petri cell culture dish.

In one embodiment of any one aspect described herein, the solid support is a porous solid support.

In one embodiment of any one aspect described herein, the solid support is a semi-permeable membrane, e.g., of a transwell.

In one embodiment of any one aspect described herein, the solid support is coated to support the adhesion, growth and differentiation of the PSCs to BMVECs under in vitro conditions. For example, coated with a matrix material. Exemplary supportive matrices include but are not limited to collagen, fibronectin, laminin, poly-D-lysine and extracellular matrix (ECM) preparations such as MATRIGEL™.

In one embodiment of any one aspect described herein, the low oxygen tension or low oxygen condition or hypoxia or hypoxic condition used in the differentiation process of PSCs to BMVECs described in this disclosure include but is not limited to about 1% $O_2$, about 2% $O_2$, about 3% $O_2$, about 4% $O_2$, about 6% $O_2$, about 7% $O_2$, about 8% $O_2$, about 9% $O_2$, about 10% $O_2$, about 11% $O_2$, about 12% $O_2$, about 13% $O_2$, about 14% $O_2$, about 15% $O_2$, about 16% $O_2$, about 17% $O_2$, about 18% $O_2$, and about 19% $O_2$.

As used herein, the terms low oxygen tension, low oxygen condition, hypoxia and hypoxic condition are used interchangeably.

In one embodiment of any one aspect described herein, the low oxygen tension used in the differentiation process is at least less than 20% $O_2$, at least less than 19% $O_2$, at least less than 18% $O_2$, at least less than 17% $O_2$, at least less than 16% $O_2$, at least less than 15% $O_2$, at least less than 14% $O_2$, at least less than 13% $O_2$, at least less than 12% $O_2$, at least less than 11% $O_2$, at least less than 10% $O_2$, at least less than 9% $O_2$, at least less than 8% $O_2$, at least less than 7% $O_2$, at least less than 6% $O_2$, at least less than 5% $O_2$, at least less than 4% $O_2$, at least less than 3% $O_2$, and at least less than 2% $O_2$.

In one embodiment of any one aspect described herein, the low oxygen tension used in the differentiation process is between 2% to 19% $O_2$, between 2% to 18% $O_2$, between 2% to 17% $O_2$, between 2% to 16% $O_2$, between 2% to 15% $O_2$, between 2% to 14% $O_2$, between 2% to 13% $O_2$, between 2% to 12% $O_2$, between 2% to 11% $O_2$, between 2% to 10% $O_2$, between 2% to 9% $O_2$, between 2% to 8% $O_2$, between 2% to 7% $O_2$, between 2% to 6% $O_2$, between 2% to 5% $O_2$, between 2% to 4% $O_2$, between 3% to 19% $O_2$, between 3% to 18% $O_2$, between 3% to 16% $O_2$, between 3% to 15% $O_2$, between 3% to 14% $O_2$, between 3% to 13% $O_2$, between 3% to 12% $O_2$, between 3% to 11% $O_2$, between 3% to 10% $O_2$, between 3% to 9% $O_2$, between 3% to 8% $O_2$, between 3% to 7% $O_2$, between 3% to 6% $O_2$, between 3% to 5% $O_2$, between 3% to 4% $O_2$, between 4% to 19% $O_2$, between 4% to 18% $O_2$, between 4% to 16% $O_2$, between 4% to 15% $O_2$, between 4% to 14% $O_2$, between 4% to 13% $O_2$, between 4% to 12% $O_2$, between 4% to 11% $O_2$, between 4% to 10% $O_2$, between 4% to 9% $O_2$, between 4% to 8% $O_2$, between 4% to 7% $O_2$, between 4% to 6% $O_2$, between 4% to 5% $O_2$, between 5% to 19% $O_2$, between 5% to 18% $O_2$, between 5% to 16% $O_2$, between 5% to 15% $O_2$, between 5% to 14% $O_2$, between 5% to 13% $O_2$, between 5% to 12% $O_2$, between 5% to 11% $O_2$, between 5% to 10% $O_2$, between 5% to 9% $O_2$, between 5% to 8% $O_2$, between 5% to 7% $O_2$, between 5% to 6% $O_2$, between 6% to 19% $O_2$, between 6% to 18% $O_2$, between 6% to 16% $O_2$, between 6% to 15% $O_2$, between 6% to 14% $O_2$, between 6% to 13% $O_2$, between 6% to 12% $O_2$, between 6% to 11% $O_2$, between 6% to 10% $O_2$, between 6% to 9% $O_2$, between 6% to 8% $O_2$, between 6% to 7% $O_2$, between 7% to 19% $O_2$, between 7% to 18% $O_2$, between 7% to 16% $O_2$, between 7% to 15% $O_2$, between 7% to 14% $O_2$, between 7% to 13% $O_2$, between 7% to 12% $O_2$, between 7% to 11% $O_2$, between 7% to 10% $O_2$, between 7% to 9% $O_2$, between 7% to 8% $O_2$, between 8% to 19% $O_2$, between 8% to 18% $O_2$, between 8% to 16% $O_2$, between 8% to 15% $O_2$, between 8% to 14% $O_2$, between 8% to 13% $O_2$, between 8% to 12% $O_2$, between 8% to 11% $O_2$, between 8% to 10% $O_2$, and between 8% to 9% $O_2$.

In one embodiment of any one aspect described herein, the normal oxygen condition or normoxia, or normoxic condition described in this disclosure is 20% $O_2$.

As used herein, the terms normal oxygen condition, normoxia, and normoxic condition are used interchangeably.

In one embodiment of any one aspect described herein, the period of time during differentiation of the PSCs where the PSCs are under low oxygen tension or low oxygen condition or hypoxia or hypoxic condition is about 1 day, about 2 days, about 3 days, about 4 days, about 5 days, about 6 days, about 7 days, about 8 days, about 9 days, about 10 days, about 11 days, about 12 days, about 13 days, about 14 days, and up to about 15 days before being returned to normoxic conditions.

In one embodiment of any one aspect described herein, the period of time during differentiation of the PSCs where the PSCs are under low oxygen tension is at least 1 day, at least 2 days, at least 3 days, at least 4 days, at least 5 days, at least 6 days, at least 7 days, at least 8 days, at least 9 days, at least 10 days before being returned to normoxic conditions.

In one embodiment of the method described herein, the period of time during differentiation of the PSCs where the PSCs are under low oxygen tension is between 1 day to 15 days, between 1 day to 14 days, between 1 day to 13 days, between 1 day to 12 days, between 1 day to 11 days, between 1 day to 10 days, between 1 day to 9 days, between 1 day to 8 days, between 1 day to 7 days, between 1 day to 6 days, between 1 day to 5 days, between 1 day to 4 days, between 1 day to 3 days, between 1 day to 2 days, between 2 days to 15 days, between 2 days to 14 days, between 2 days to 13 days, between 2 days to 12 days, between 2 days to 11 days, between 2 days to 10 days, between 2 days to 9 days, between 2 days to 8 days, between 2 days to 7 days, between 2 days to 6 days, between 2 days to 5 days, between 2 days to 4 days, between 2 days to 3 days, between 3 days to 15 days, between 3 days to 14 days, between 3 days to 13 days, between 3 days to 12 days, between 3 days to 11 days, between 3 days to 10 days, between 3 days to 9 days, between 3 days to 8 days, between 3 days to 7 days, between 3 days to 6 days, between 3 days to 5 days, between 3 days to 4 days, between 4 days to 15 days, between 4 days to 14 days, between 4 days to 13 days, between 4 days to 12 days, between 4 days to 11 days, between 4 days to 10 days, between 4 days to 9 days, between 4 days to 8 days, between 4 days to 7 days, between 4 days to 6 days, between 4 days to 5 days, between 5 days to 15 days, between 5 days to 14 days, between 5 days to 13 days, between 5 days to 12 days, between 5 days to 11 days, between 5 days to 10 days, between 5 days to 9 days, between 5 days to 8 days, between 5 days to 7 days, between 5 days to 6 days, between 6 days to 15 days, between 6 days to 14 days, between 6 days to 13 days, between 6 days to 12 days, between 6 days to 11 days, between 6 days to 10 days, between 6 days to 9 days, between 6 days to 8 days, between 6 days to 7 days, between 7 days to 15 days, between 7 days to 14 days, between 7 days to 13 days, between 7 days to 12 days, between 7 days to 11 days, between 7 days to 10 days, between 6 days to 9 days, between 7 days to 8 days, between 8 days to 15 days, between 8 days to 14 days, between 8 days to 13 days, between 8 days to 12 days, between 8 days to 11 days, between 8 days to 10 days, between 8 days to 9 days, between 9 days to 15 days, between 9 days to 14 days, between 9 days to 13 days, between 9 days to 12 days, between 9 days to 11 days, between 9 days to 10 days, between 10 days to 15 days, between 10 days to 14 days, between 10 days to 13 days, between 10 days to 12 days, between 10 days to 11 days, between 11 days to 15 days, between 11 days to 12 days, between 12 days to 15 days, between 12 days to 14 days, between 13 days to 15 days, or between 14 days to 15 days before being returned to normoxic conditions.

In one embodiment of any one aspect described herein, the unconditional medium that supports the differentiation of PSCs to BMVECs does not comprise human basic fibroblast growth factor (bFGF). In one embodiment of any one aspect described herein, the unconditional medium that supports the differentiation of PSCs to BMVECs comprises RA.

In one embodiment of any one aspect described herein, the medium comprising RA for differentiating the PSCs comprises at least 10 µM RA.

In one embodiment of any one aspect described herein, the RA in the medium is at least 1 RA, at least 2 µM RA, at least 3 µM RA, at least 4 µM RA, at least 5 µM RA, at least 6 µM RA, at least 7 µM RA, at least 8 µM RA, at least 9 µM RA, at least 11 µm RA, at least 12 µM RA, at least 13 µM RA, at least 14 µM RA, at least 15 µM RA, at least 16 µM RA, at least 17 µM RA, at least 18 µM RA, at least 19 µM RA, or at least 20 µM RA.

In one embodiment of any one aspect described herein, the RA is about 1 µM-20 uM, 2 uM-20 uM, 3 uM-20 uM, 4 uM-20 uM, 5 uM-20 uM, 6 uM-20 uM, 7 uM-20 uM, 8 uM-20 uM, 9 uM-20 uM, 10 uM-20 uM, 11 uM-20 uM, 12 uM-20 uM, 13 uM-20 uM, 14 uM-20 uM, 15 vM-20 uM, 1 uM-18 uM, 1 uM-16 uM, 1 uM-14 uM, 1 M-12 uM, 1 M-10 uM, 2 uM-20 uM, 2 uM-18 uM, 2 uM-16 uM, 2 uM-14 uM, 2 uM-12 uM, 2 uM-10 uM, 4 uM-20 uM, 4 uM-18 uM, 4 uM-16 uM, 4 uM-14 uM, 4 uM-12 uM, 4 uM-10 uM, 6 uM-20 uM, 6 uM-18 uM, 6 uM-16 uM, 6 uM-14 uM, 6 uM-12 uM, 6 uM-10 uM, 8 uM-20 uM, 8 uM-18 uM, 8 uM-16 uM, 8 uM-14 uM, 8 uM-12 uM, 8 uM-10 uM, 10 uM-20 uM, 10 uM-18 uM, 10 uM-16 uM, 10 uM-14 uM, 10 M-12 uM, 12 uM-20 uM, 12 uM-18 uM, 12 uM-16 uM, 12 uM-14 uM, 14 uM-20 uM, 14 uM-18 uM, 14 uM-16 uM, 16 uM-20 uM, or 16 uM-18 uM.

In one embodiment of any one aspect described herein, the PSCs used for deriving the BMVECs are induced pluripotent stem cells (iPSCs) or embryonic stem cells (ESC).

In one embodiment of the method described herein, the PSCs used for deriving the BMVECs are mammalian PSCs.

In one embodiment of any one aspect described herein, the PSCs used for deriving the BMVECs are primate PSCs.

In one embodiment of any one aspect described herein, the PSCs used for deriving the BMVECs are human PSCs.

In one embodiment of any one aspect described herein, the iPSCs used for deriving the BMVECs are produced by introducing only reprogramming factors OCT4, SOX2, KLF4 and optionally c-MYC or nanog and LIN28 into mature cells.

In one embodiment of any one aspect described, the mature cells for producing iPS cells are selected from the group consisting of B lymphocytes (B-cells), T lymphocytes, (T-cells), fibroblasts, and keratinocytes.

In one embodiment of any one aspect described, the induced pluripotent stem cells are produced by introducing the reprogramming factors two or more times into the mature cells.

In one embodiment of any one aspect described, the BMVECs are iPSC-derived and differentiated under low oxygen levels.

In one embodiment of any one aspect described, the TEER value is sustained at 2000 Ω·cm² or greater for at least three days in culture.

In one embodiment of any one aspect described, the TEER value is greater than 2000 Ω·cm² at day three of culture.

In one embodiment of any one aspect described, the TEER value is greater than 2500 Ω·cm² at day four of culture. The TEER can be measured by any method known in the art. For example, as described in the Example section of this disclosure.

In one embodiment of any one aspect described, the TEER value is greater than 2100, 2200, 2300, 2400, 2500, 2600, 2700, 2800, 2900, 3000 Ω·cm² at day three of culture.

In one embodiment of any one aspect described, the TEER value is about 2100, 2200, 2300, 2400, 2500, 2600, 2700, 2800, 2900, 3000, 3100, 3200, 3300, 3400, 3500, 3600, 3700, 3800, 3900, or 4000 Ω·cm² at day three of culture.

In one embodiment of any one aspect described, the cells are selected from the group consisting of stem cells, cells differentiated from stem cells and primary cells.

In one embodiment of any one aspect described, the cells differentiated from stem cells are brain microvascular endothelial cells.

In one embodiment of any one aspect described, the BMVECs are GLUT-1+.

In one embodiment of any one aspect described, the BMVECs are GLUT-1+, PECAM-1+, claudin-5+, occludin+, ZO-1+ and p-glycoprotein+.

In one embodiment of any one aspect described, the BMVECs are Z0-1+, occludin+, JAM-A+, claudin-5+, claudin-3+, claudin-1+.

In one embodiment of any one aspect described, the BMVECs are ZO-1+ and/or claudin-1+.

In one embodiment of any one aspect described, the BMVECs are positively expressing at least one of the following transporters or receptors: amino acid-SLC7A5, SLC16A1, glucose-SLC2A1.

In one embodiment of any one aspect described, the BMVECs are von Willebrand factor+ and VE-cadherin+.

In one embodiment of any one aspect described, the BMVECs are positively expressing at least one of the following molecules: CD40, VCAM-1.

In one embodiment of any one aspect described, the BMVECs are positively expressing at least one of the following transcripts of key efflux transporters as P-glycoprotein, breast cancer resistance protein and multidrug resistance protein.

In one embodiment of any one aspect described, the BMVECs are positively expressing at least one of the following genes up-regulated: SLC44A5, SLC25A27, SLC23A3.

In one embodiment of any one aspect described, the BMVECs are positively expressing at least one of the following markers: lipoprotein receptor, insulin receptor, leptin receptor, transferrin receptor, receptor for advanced glycation endproducts, retinol binding protein, SLC38A5, ABCB1, ABCG2, ABCC1, ABCC2, ABCC4, ABCC5.

In one embodiment of any one aspect described, the BMVECs are grown to confluence on the membrane or on the surface or solid support.

In one embodiment of any one aspect described, the pericytes or astrocytes are grown to confluence on the membrane or on the surface or solid support.

In one embodiment of any one aspect described, the low oxygen conditions comprise less than 10% oxygen.

In one embodiment of any one aspect described, the low oxygen conditions comprise approximately 5% oxygen.

In one embodiment of any one aspect described, the cells are grown on solid support or surface.

In one embodiment of any one aspect described, the surface comprises extracellular matrix proteins.

the cells are seeded onto a solid surface coated with extracellular matrix proteins.

In one embodiment, the method further comprising the step of growing any of the cells described herein to confluence.

In one embodiment of any one aspect described, the method further comprising the step of growing the BMVECs to confluence, wherein a blood brain barrier model is obtained.

In one embodiment of any one aspect described, the cells are grown to confluence on a solid support, wherein the cells are von Willebrand factor+ and VE-cadherin+, and wherein a blood brain barrier is obtained.

In one embodiment of any one aspect described, the human stem cells are human pluripotent stem cells.

In one embodiment of any one aspect described, the human stem cells are isolated from cord blood or peripheral blood.

In one embodiment of any one aspect described, the human stem cells are induced pluripotent stem cells (iPSCs).

In one embodiment of any one aspect described, the iPSCs are derived from a human patient.

In one embodiment of any one aspect described, the human stem cells are CD34+.

In one embodiment of any one aspect described, the method described herein comprising co-culturing the BMVECs with a cell type selected from the group consisting of astrocytes, pericytes and differentiated neural progenitor cells (NPCs), so as to create a BBB model in vitro.

Pericytes refers to cells that express one of the following markers: vimentin, neuro-glial 2 (NG2), platelet-derived growth factor receptor beta (PDGFR-β), and α-smooth muscle actin (α-SMA). In one embodiment of any one aspect described, the co-culturing is with at least two cell types from the group.

In one embodiment of any one aspect described, seeding the BMVECs on transwells or on a microfluidic device having flow.

Induced Pluripotent Stem Cells

In some embodiments, the pluripotent stem cells (PSCs) described herein are derived from isolated induced pluripotent stem cells (iPSCs). The use of iPSCs negates the need for cells obtained from an embryonic source. Thus, in one embodiment, the PSCs used in the disclosed methods are not embryonic stem cells.

Although differentiation is generally irreversible under physiological contexts, several methods have been recently developed to reprogram somatic cells to induced pluripotent stem cells. Exemplary methods are known to those of skill in the art and are described briefly herein below.

As used herein, the term "reprogramming" refers to a process that alters or reverses the differentiation state of a differentiated cell (e.g., a somatic cell). Stated another way, reprogramming refers to a process of driving the differentiation of a cell backwards to a more undifferentiated or more primitive type of cell. It should be noted that placing many primary cells in culture can lead to some loss of fully differentiated characteristics. Thus, simply culturing such cells included in the term differentiated cells does not render these cells non-differentiated cells (e.g., undifferentiated cells) or pluripotent cells. The transition of a differentiated cell to pluripotency requires a reprogramming stimulus beyond the stimuli that lead to partial loss of differentiated character in culture. Reprogrammed cells also have the characteristic of the capacity of extended passaging without loss of growth potential, relative to primary cell parents, which generally have capacity for only a limited number of divisions in culture.

The cell to be reprogrammed can be either partially or terminally differentiated prior to reprogramming. In some embodiments, reprogramming encompasses complete reversion of the differentiation state of a differentiated cell (e.g., a somatic cell) to a pluripotent state or a multipotent state. In some embodiments, reprogramming encompasses complete or partial reversion of the differentiation state of a differentiated cell (e.g., a somatic cell) to an undifferentiated cell (e.g., an embryonic-like cell). Reprogramming can result in expression of particular genes by the cells, the expression of which further contributes to reprogramming. In certain embodiments described herein, reprogramming of a differentiated cell (e.g., a somatic cell) causes the differentiated cell to assume an undifferentiated state (e.g., is an undifferentiated cell). The resulting cells are referred to as "reprogrammed cells," or "induced pluripotent stem cells (iPSCs or iPS cells)."

Reprogramming can involve alteration, e.g., reversal, of at least some of the heritable patterns of nucleic acid modification (e.g., methylation), chromatin condensation, epigenetic changes, genomic imprinting, etc., that occur during cellular differentiation. Reprogramming is distinct from simply maintaining the existing undifferentiated state of a cell that is already pluripotent or maintaining the existing less than fully differentiated state of a cell that is already a multipotent cell (e.g., a common myeloid stem cell). Reprogramming is also distinct from promoting the self-renewal or proliferation of cells that are already pluripotent or multipotent, although the compositions and methods described herein can also be of use for such purposes, in some embodiments.

The specific approach or method used to generate pluripotent stem cells from somatic cells (broadly referred to as "reprogramming") is not critical to the claimed invention. Thus, any method that re-programs a somatic cell to the pluripotent phenotype would be appropriate for use in the methods described herein.

Reprogramming methodologies for generating pluripotent cells using defined combinations of transcription factors have been described to induced pluripotent stem cells from somatic cells. Yamanaka and Takahashi converted mouse somatic cells to ES cell-like cells with expanded developmental potential by the direct transduction of Oct4, Sox2, Klf4, and optionally c-Myc. See U.S. Pat. Nos. 8,058,065 and 9,045,738 to Yamanaka and Takahashi. iPSCs resemble ES cells as they restore the pluripotency-associated transcriptional circuitry and much of the epigenetic landscape. In addition, mouse iPSCs satisfy all the standard assays for pluripotency: specifically, in vitro differentiation into cell types of the three germ layers, teratoma formation, contribution to chimeras, germline transmission, and tetraploid complementation.

Subsequent studies have shown that human iPS cells can be obtained using similar transduction methods, and the transcription factor trio, OCT4, SOX2, and NANOG, has been established as the core set of transcription factors that govern pluripotency. The production of iPS cells can be achieved by the introduction of nucleic acid sequences encoding stem cell-associated genes into an adult, somatic cell, using viral vectors.

iPS cells can be generated or derived from terminally differentiated somatic cells, as well as from adult stem cells, or somatic stem cells. That is, a non-pluripotent progenitor cell can be rendered pluripotent or multipotent by reprogramming. In such instances, it may not be necessary to include as many reprogramming factors as required to reprogram a terminally differentiated cell. Further, reprogramming can be induced by the non-viral introduction of reprogramming factors, e.g., by introducing the proteins themselves, or by introducing nucleic acids that encode the reprogramming factors, or by introducing messenger RNAs that upon translation produce the reprogramming factors (see e.g., Warren et al., Cell Stem Cell, 2010 Nov. 5; 7(5):618-30, this reference is incorporated herein by reference in its entirety.). Reprogramming can be achieved by introducing a combination of nucleic acids encoding stem cell-associated genes including, for example Oct-4 (also known as Oct-3/4 or Pouf51), Sox1, Sox2, Sox3, Sox 15, Sox 18, NANOG, Klf1, Klf2, Klf4, Klf5, NR5A2, c-Myc, 1-Myc, n-Myc, Rem2, Tert, and LIN28. In one embodiment, reprogramming using the methods and compositions described herein can further comprise introducing one or more of Oct-3/4, a member of the Sox family, a member of the Klf family, and a member of the Myc family to a somatic cell. In one embodiment, the methods and compositions described herein further comprise introducing one or more of each of Oct 4, Sox2, Nanog, c-MYC and Klf4 for reprogramming. As noted above, the exact method used for reprogramming is not necessarily critical to the methods and compositions described herein. However, where cells differentiated from the reprogrammed cells are to be used in, e.g., human therapy, in one embodiment the reprogramming is not effected by a method that alters the genome. Thus, in such embodiments, reprogramming is achieved, e.g., without the use of viral or plasmid vectors.

The efficiency of reprogramming (i.e., the number of reprogrammed cells) derived from a population of starting cells can be enhanced by the addition of various small molecules as shown by Shi, Y., et al (2008) Cell-Stem Cell 2:525-528, Huangfu, D., et al (2008) Nature Biotechnology 26(7):795-797, and Marson, A., et al (2008) Cell-Stem Cell 3:132-135. This reference is incorporated herein by reference in its entirety. Thus, an agent or combination of agents that enhance the efficiency or rate of induced pluripotent stem cell production can be used in the production of patient-specific or disease-specific iPSCs. Some non-limiting examples of agents that enhance reprogramming efficiency include soluble Wnt, Wnt conditioned media, BIX-01294 (a G9a histone methyltransferase), PD0325901 (a MEK inhibitor), DNA methyltransferase inhibitors, histone deacetylase (HDAC) inhibitors, valproic acid, 5'-azacytidine, dexamethasone, suberoylanilide hydroxamic acid (SAHA), vitamin C, and trichostatin (TSA), among others.

Other non-limiting examples of reprogramming enhancing agents include: Suberoylanilide Hydroxamic Acid (SAHA (e.g., MKO683, vorinostat) and other hydroxamic acids), BML-210, Depudecin (e.g., (−)-Depudecin), HC Toxin, Nullscript (4-(1,3-Dioxo-1H,3H-benzo[de]isoquinolin-2-yl)-N-hydroxybutanamide), Phenylbutyrate (e.g., sodium phenylbutyrate) and Valproic Acid ((VPA) and other short chain fatty acids), Scriptaid, Suramin Sodium, Trichostatin A (TSA), APHA Compound 8, Apicidin, Sodium Butyrate, pivaloyloxymethyl butyrate (Pivanex, AN-9), Trapoxin B, Chlamydocin, Depsipeptide (also known as FR901228 or FK228), benzamides (e.g., CI-994 (e.g., N-acetyl dinaline) and MS-27-275), MGCD0103, NVP-LAQ-824, CBHA (m-carboxycinnaminic acid bishydroxamic acid), JNJ16241199, Tubacin, A-161906, proxamide, oxamflatin, 3-Cl-UCHA (e.g., 6-(3-chlorophenylureido) caproic hydroxamic acid), AOE (2-amino-8-oxo-9,10-epoxydecanoic acid), CHAP31 and CHAP 50. Other reprogramming enhancing agents include, for example, dominant negative forms of the HDACs (e.g., catalytically inactive forms), siRNA inhibitors of the HDACs, and antibodies that specifically bind to the HDACs. Such inhibitors are available, e.g., from BIOMOL International, Fukasawa, Merck Biosciences, Novartis, Gloucester Pharmaceuticals, Aton Pharma, Titan Pharmaceuticals, Schering AG, Pharmion, MethylGene, and Sigma Aldrich.

To confirm the induction of pluripotent stem cells for use with the methods described herein, isolated clones can be tested for the expression of a stem cell marker. Such expression in a cell derived from a somatic cell identifies the cells as induced pluripotent stem cells. Stem cell markers can be selected from the non-limiting group including SSEA3, SSEA4, CD9, Nanog, Fbx15, Ecat1, Esg1, Eras, Gdf3, Fgf4, Cripto, Dax1, Zpf296, Slc2a3, Rex1, Utf1, and Nat1. In one embodiment, a cell that expresses Oct4 or Nanog is identified as pluripotent. Methods for detecting the expression of such markers can include, for example, RT-PCR and immunological methods that detect the presence of the encoded polypeptides, such as Western blots or flow cytometric analyses. In some embodiments, detection does not involve only RT-PCR, but also includes detection of protein markers. Intracellular markers may be best identified via RT-PCR, while cell surface markers are readily identified, e.g., by immunocytochemistry.

The pluripotent stem cell character of isolated cells can be confirmed by tests evaluating the ability of the iPSCs to differentiate to cells of each of the three germ layers. As one example, teratoma formation in nude mice can be used to evaluate the pluripotent character of the isolated clones. The cells are introduced to nude mice and histology and/or immunohistochemistry is performed on a tumor arising from the cells. The growth of a tumor comprising cells from all three germ layers, for example, further indicates that the cells are pluripotent stem cells.

Many US Patents and Patent Application Publications teach and describe methods of generating iPSCs and related subject matter. For examples, U.S. Pat. Nos. 9,347,044, 9,347,042, 9,347,045, 9,340,775, 9,341,625, 9,340,772, 9,250,230, 9,132,152, 9,045,738, 9,005,975, 9,005,976, 8,927,277, 8,993,329, 8,900,871, 8,852,941, 8,802,438, 8,691,574, 8,735,150, 8,765,470, 8,058,065, 8,048,675, and US Patent Publication Nos: 20090227032, 20100210014, 20110250692, 20110201110, 20110200568, 20110306516, 20100021437, 20110256626, 20110044961, 20120276070, 20120263689, 20120128655, 20120100568, 20130295064, 20130029866, 20130189786, 20130295579, 20130130387, 20130157365, 20140234973, 20140227736, 20140093486, 20140301988, 20140170746, 20140178989, 20140349401, 20140065227, and 20150140662. These references are incorporated herein by reference in their entirety.

Somatic Cells for Reprogramming

Somatic cells, as that term is used herein, refer to any cells forming the body of an organism, excluding germline cells. Every cell type in the mammalian body—apart from the sperm and ova, the cells from which they are made (gametocytes) and undifferentiated stem cells—is a differentiated somatic cell. For example, internal organs, skin, bones, blood, and connective tissue are all made up of differentiated somatic cells.

Additional somatic cell types for use with the compositions and methods described herein include: a fibroblast (e.g., a primary fibroblast), a muscle cell (e.g., a myocyte), a cumulus cell, a neural cell, a mammary cell, an hepatocyte and a pancreatic islet cell. In some embodiments, the somatic cell is a primary cell line or is the progeny of a primary or secondary cell line. In some embodiments, the somatic cell is obtained from a human sample, e.g., a hair follicle, a blood sample, a biopsy (e.g., a skin biopsy or an adipose biopsy), a swab sample (e.g., an oral swab sample), and is thus a human somatic cell.

Some non-limiting examples of differentiated somatic cells include, but are not limited to, epithelial, endothelial, neuronal, adipose, cardiac, skeletal muscle, skin, immune cells, hepatic, splenic, lung, peripheral circulating blood cells, gastrointestinal, renal, bone marrow, and pancreatic cells. In some embodiments, a somatic cell can be a primary cell isolated from any somatic tissue including, but not limited to brain, liver, gut, stomach, intestine, fat, muscle, uterus, skin, spleen, endocrine organ, bone, etc. Further, the somatic cell can be from any mammalian species, with non-limiting examples including a murine, bovine, simian, porcine, equine, ovine, or human cell. In some embodiments, the somatic cell is a human somatic cell.

When reprogrammed cells are used for generation of thyroid progenitor cells to be used in the therapeutic treatment of disease, it is desirable, but not required, to use somatic cells isolated from the patient being treated. For example, somatic cells involved in diseases, and somatic cells participating in therapeutic treatment of diseases and the like can be used. In some embodiments, a method for selecting the reprogrammed cells from a heterogeneous population comprising reprogrammed cells and somatic cells they were derived or generated from can be performed by any known means. For example, a drug resistance gene or the like, such as a selectable marker gene can be used to isolate the reprogrammed cells using the selectable marker as an index.

Reprogrammed somatic cells as disclosed herein can express any number of pluripotent cell markers, including: alkaline phosphatase (AP); ABCG2; stage specific embryonic antigen-1 (SSEA-1); SSEA-3; SSEA-4; TRA-1-60; TRA-1-81; Tra-2-49/6E; ERas/ECAT5, E-cadherin; β-III-tubulin; α-smooth muscle actin (α-SMA); fibroblast growth factor 4 (Fgf4), Cripto, Dax1; zinc finger protein 296 (Zfp296); N-acetyltransferase-1 (Nat1); (ES cell associated transcript 1 (ECAT1); ESG1/DPPA5/ECAT2; ECAT3; ECAT6; ECAT7; ECAT8; ECAT9; ECAT10; ECAT15-1; ECAT15-2; Fthl17; Sal14; undifferentiated embryonic cell transcription factor (Utf1); Rex1; p53; G3PDH; telomerase, including TERT; silent X chromosome genes; Dnmt3a; Dnmt3b; TRIM28; F-box containing protein 15 (Fbx15); Nanog/ECAT4; Oct3/4; Sox2; Klf4; c-Myc; Esrrb; TDGF1; GABRB3; Zfp42, FoxD3; GDF3; CYP25A1; developmental pluripotency-associated 2 (DPPA2); T-cell lymphoma breakpoint 1 (Tcl1); DPPA3/Stella; DPPA4; other general markers for pluripotency, etc. Other markers can include Dnmt3L; Sox15; Stat3; Grb2; β-catenin, and Bmi1. Such cells can also be characterized by the down-regulation of markers characteristic of the somatic cell from which the induced pluripotent stem cell is derived.

The present invention can be defined in any of the following paragraphs:

[1] A method for producing human brain-like endothelial cells (BMVECs) comprising a) contacting a population of human stem cells or PSCs with a medium to support differentiation of the PSCs to BMVECs, b) exposing the PSCs to conditions of low oxygen tension for a period of time to obtain the BMVECs, and c) returning the cells to normal oxygen tension.

[2] A method for making BMVECs from PSCs comprising exposing a population of PSCs to conditions of low oxygen tension for a period of time and in a medium that support differentiation of the PSCs to BMVECs, and returning the cells to normal oxygen tension.

[3] A method of producing BMVECs from human stem cells or PSCs wherein the BMVECs exhibit improved BBB characteristics in culture such as sustained high TEER of the barrier, the method comprises providing a) a population of human stem cells or PSCs, b) contacting the population of human stem cells or PSCs with a medium to support differentiation of the PSCs to BMVECs under conditions of low oxygen tension for a period of time, c) contacting the cells of step b to a medium comprising RA under conditions of low oxygen tension for a period of time, and d) returning the cells to normal oxygen tension.

[4] A method of BMVECs culturing cells, comprising: a) providing a microfluidic device comprising a membrane, the membrane comprising a top surface and a bottom surface; b) seeding BMVECs cells on the bottom surface; and c) culturing the seeded BMVECs cells under low oxygen conditions that support the maturation of BMVECs.

[5] A method of generating BMVECs, comprising the steps of: a) growing human stem cells or PSCs on a surface or solid support; b) inducing differentiation of the cells by culturing the cells in an unconditioned medium under conditions of low oxygen tension for a period of time; and c) continuing differentiation of the cells by culturing the cells in medium comprising retinoic acid (RA) again under conditions of low oxygen, so as to produce BMVECs.

[6] A method of producing BMVECs, comprising the steps of: a) growing human stem cells or PSCs on a surface or solid support; b) inducing differentiation of the cells by culturing the cells in unconditioned medium that supports support differentiation of the PSCs to BMVECs; and c) exposing the cells to low oxygen conditions for a period of time during the differentiation process so as to produce BMVECs.

[7] A method of generating BMVECs, comprising the steps of: a) growing human stem cells or PSCs on a surface or solid support; b) inducing differentiation of the cells by culturing the cells in unconditioned medium; c) exposing the cells to low oxygen conditions, and d) expanding the cells under the low oxygen conditions by culturing the cells in EC medium, the EC medium comprising RA, so as to produce BMVECs.

[8] A method of generating BMVECs, comprising the steps of: a) growing human stem cells or PSCs on a surface or solid support; b) inducing differentiation of the cells by culturing the cells in unconditioned medium under conditions of low oxygen tension; c) expanding the cells by culturing the cells in EC medium, the EC medium comprising retinoic acid (RA) under conditions of low oxygen tension, so as to produce brain microvascular endothelial cells (BMVECs).

[9] A population of BMVECs generated by any of the method described herein that TEER values of greater than 2000 $\Omega \cdot cm^2$ for at least three days of culture when grown to confluence in culture.

[10] A composition comprising a population of BMVECs generated by any of the method described herein.

[11] A method of creating a blood-brain barrier (BBB) model, comprising the steps of: a) providing a population of BMVECs that are cultured differentiated under low oxygen conditions described herein, wherein the BMVECs are from the differentiation of pluripotent stem cells (PSCs); b) providing a mixture of neural cells such as astrocytes, pericytes, and neural progenitor cells; c) co-culturing the BMVECs with a cell type selected from the group consisting of pericytes, astrocytes and differentiated neural progenitor cells (NPCs) to confluence, wherein a blood brain barrier model is created.

[12] A method of creating an improved mammalian blood-brain barrier (BBB) model that has TEER values of greater than 2000 $\Omega \cdot cm^2$ for at least three days of culture, comprising the steps of: a) providing a population of BMVECs that are cultured differentiated under low oxygen conditions described herein, wherein the BMVECs are from the differentiation of pluripotent stem cells (PSCs); b) providing a mixture of neural cells such as astrocytes, pericytes, and neural progenitor cells; c) co-culturing the BMVECs with a cell type selected from the group consisting of pericytes, astrocytes and differentiated neural progenitor cells (NPCs) to confluence, wherein a blood brain barrier model is created.

[13] A method of creating an improved mammalian blood-brain barrier (BBB) model that has TEER values of greater than 2000 $\Omega \cdot cm^2$ for at least three days of culture, comprising the steps of: a) providing a population of BMVECs that are cultured differentiated under low oxygen conditions described herein, wherein the BMVECs are from the differentiation of a population of human stem cell or pluripotent stem cells (PSCs) by (i) contacting the population of human stem cells or PSCs with a medium to support differentiation of the PSCs to BMVECs, (ii) exposing the cells to conditions of low oxygen tension for a period of time, (iii) contacting the cells of step b to a medium comprising RA under continued conditions of low oxygen tension for a period of time, and (iv) returning the cells to normal oxygen tension; b) providing a mixture of neural cells such as astrocytes, pericytes, and neural progenitor cells; c) co-culturing the BMVECs with a cell type selected from the group consisting of pericytes, astrocytes and differentiated neural progenitor cells (NPCs) to confluence, wherein a blood brain barrier model is created.

[14] A blood-brain barrier (BBB) model created by the method of creating an improved blood-brain barrier (BBB) model that has TEER values of greater than 2000 $\Omega \cdot cm^2$ for at least three days of culture, the method comprising the steps of: a) providing a population of BMVECs that are cultured differentiated under low oxygen conditions described herein, wherein the BMVECs are from the differentiation of pluripotent stem cells (PSCs); b) providing a mixture of neural cells such as astrocytes, pericytes, and neural progenitor cells; c) co-culturing the BMVECs with a cell type selected from the group consisting of pericytes, astrocytes and differentiated neural progenitor cells (NPCs) to confluence, wherein a blood brain barrier model is created.

[15] An apparatus comprising a membrane, the membrane comprising BMVECs that are cultured differentiated under low oxygen conditions described herein.

[16] An apparatus comprising a monoculture of BMVECs are cultured differentiated under low oxygen conditions described herein and the cells displaying TEER values of greater than 2000 $\Omega \cdot cm^2$ for at least three days of culture.

[17] An apparatus having a membrane comprising a co-culture of BMVECs and astrocytes and pericytes, the co-culture displaying TEER values of greater than 2000 $\Omega \cdot cm^2$ for at least three days of culture.

[18] A microfluidic device comprising a membrane, the membrane comprising BMVECs that are cultured differentiated under low oxygen conditions described herein.

[19] A microfluidic device comprising a monoculture of BMVECs are cultured differentiated under low oxygen conditions described herein and the cells displaying TEER values of greater than 2000 $\Omega \cdot cm^2$ for at least three days of culture.

[20] A microfluidic device having a membrane comprising a co-culture of BMVECs and astrocytes and pericytes, the co-culture displaying TEER values of greater than 2000 $\Omega \cdot cm^2$ for at least three days of culture.

[21] A transwell comprising a membrane, separating the transwell into two compartments, an apical (top) chamber and a basal (bottom) chamber, the transwell comprising BMVECs that are cultured differentiated under low oxygen conditions described herein.

[22] A transwell having a membrane, the transwell comprising a monoculture of BMVECs are cultured differentiated under low oxygen conditions described herein and the cells displaying TEER values of greater than 2000 $\Omega \cdot cm^2$ for at least three days of culture, the transwell comprises a membrane which separates the transwell into two compartments, an apical (top) chamber and a basal (bottom) chamber.

[23] A transwell having a membrane comprising a co-culture of BMVECs and (i) astrocytes; or (ii) pericytes; or (iii) both astrocytes and pericytes, the co-culture displaying TEER values of greater than 2000 $\Omega \cdot cm^2$ for at least three days of culture.

[24] An in vitro BBB model comprising a microfluidic device comprising a membrane, the membrane comprising BMVECs that are cultured differentiated under low oxygen conditions described herein.

[25] An in vitro BBB model comprising a microfluidic device comprising a monoculture of BMVECs are cultured differentiated under low oxygen conditions described herein and the cells displaying TEER values of greater than 2000 $\Omega \cdot cm^2$ for at least three days of culture.

[26] An in vitro BBB model comprising a microfluidic device having a membrane comprising a co-culture of BMVECs and astrocytes and pericytes, the co-culture displaying TEER values of greater than 2000 $\Omega \cdot cm^2$ for at least three days of culture.

[27] An in vitro BBB model comprising a transwell comprising a membrane, separating the transwell into two compartments, an apical (top) chamber and a basal (bottom) chamber, the transwell comprising BMVECs that are cultured differentiated under low oxygen conditions described herein.

[28] An in vitro BBB model comprising a transwell having a membrane, the transwell comprising a monoculture of BMVECs are cultured differentiated under low oxygen conditions described herein and the cells displaying TEER values of greater than 2000 $\Omega \cdot cm^2$ for at least three days of culture.

[29] An in vitro BBB model comprising a transwell having a membrane comprising a co-culture of BMVECs and (i) astrocytes; or (ii) pericytes; or (iii) both astrocytes and pericytes, the co-culture displaying TEER values of greater than 2000 $\Omega \cdot cm^2$ for at least three days of culture. In one embodiment, the BMVECs are cultured differentiated under low oxygen conditions described herein.

[30] BMVECs made according to methods described herein for use in medicine or for in vitro testing of new drugs.

[31] A use of BMVECs made according to methods described herein for use as an in vitro model of BBB.

[32] A method for evaluating blood-brain barrier permeability of a test substance, cell or protein comprising exposing the test substance, cell or protein to the BMVECs made according to methods described herein.

[33] A method for evaluating the viability or metabolism of BBB after contact with a test substance, cell or protein which comprises the following steps: contacting a test substance, cell or protein to the BMVECs made according to methods described herein, and analyzing the viability or metabolism of the BMVECs.

[34] A method for evaluating the BBB after contact with a test substance, cell or protein which comprises the following steps: contacting a test substance, cell or protein to the BMVECs made according to methods described herein, and measuring the TEER of the BBB.

[35] A kit for measuring blood-brain barrier permeability of a substance, comprising the in vitro BMVECs made according to methods described herein.

[36] A kit comprising the in vitro BMVECs made according to methods described herein and a transwell apparatus. The kit further comprises pericytes or astrocytes or both pericytes and astrocytes.

[37] A kit comprising a microfluidic device having the in vitro BMVECs made according to methods described herein. The kit further comprises pericytes or astrocytes or both pericytes and astrocytes.

[38] A kit comprising a microfluidic device, a transwell apparatus, in vitro BMVECs made according to methods described herein, both pericytes and astrocytes.

[39] A kit comprising in vitro BMVECs made according to methods described herein, both pericytes and astrocytes.

[40] The apparatus, microfluidic device or transwell of any one of the preceding paragraphs, the BMVECs are seeded on the bottom surface of the membrane in the apparatus, microfluidic device or transwell.

[41] The apparatus, microfluidic device or transwell of any one of the preceding paragraphs, the microfluidic device further comprises pericytes or astrocytes.

[42] The apparatus, microfluidic device or transwell of any one of the preceding paragraphs, the pericytes or astrocytes or both cell types are seeded on the top surface of the membrane.

[43] The apparatus, microfluidic device or transwell of any one of the preceding paragraphs, the pericytes or astrocytes are seeded on the membrane before the BMVECs.

[44] The methods, apparatus, microfluidic device or transwell of any one of the preceding paragraphs, the BMVECs are grown to confluence.

[45] The methods, apparatus, microfluidic device or transwell of any one of the preceding paragraphs, the BMVECs are grown to confluence on the membrane.

[46] The method, apparatus, microfluidic device or transwell of any one of the preceding paragraphs, the pericytes or astrocytes are grown to confluence on the membrane.

[47] The method, apparatus, microfluidic device or transwell of any one of the preceding paragraphs, the pericytes or astrocytes are grown to confluence.

[48] The transwell of any one of the preceding paragraphs, the membrane separates the transwell into two compartments, an apical (top) chamber and a basal (bottom) chamber.

[49] The apparatus, microfluidic device or transwell of any one of the preceding paragraphs, the BMVECs are seeded on the apical chamber in the transwell.

[50] The apparatus, microfluidic device or transwell of any one of the preceding paragraphs, the apparatus, microfluidic device or transwell further comprises pericytes or astrocytes or both cell types.

[51] The transwell of any one of the preceding paragraphs, the pericytes or astrocytes or both cell types are seeded on the basal chamber of the transwell.

[52] The transwell of any one of the preceding paragraphs, the pericytes or astrocytes or both cell types are seeded on the transwell before the BMVECs.

[53] The evaluating method of any one of the preceding paragraphs, the test substance is any synthetic or natural compound or a drug.

[54] The method of any one of the preceding paragraphs, wherein is measured efflux transport, preferably in the presence or absence of inhibitors of the efflux pumps.

[55] The method of any one of the preceding paragraphs, efflux pumps are at least one of the following: cyclosporin-A, PSC-833, MK-571, KO-143, verapamil, elacridar.

[56] A microfluidic device comprising a membrane, the membrane comprising brain microvascular endothelial cells (BMVECs) cultured under low oxygen conditions.

[57] The device of any one of the preceding paragraphs, wherein the membrane comprises a top surface and a bottom surface, the bottom surface comprising the BMVECs.

[58] A microfluidic device comprising a monoculture of brain microvascular endothelial cells displaying TEER values of greater than 2000 $\Omega \cdot cm^2$ for at least three days of culture.

[59] The device of any one of the preceding paragraphs, wherein the BMVECs are iPSC-derived and differentiated under low oxygen levels.

[60] A microfluidic device comprising a co-culture of brain microvascular endothelial cells (BMVECs) and astrocytes and pericytes, the co-culture displaying TEER values of greater than 2000 $\Omega \cdot cm^2$ for at least three days of culture.

[61] The device of any one of the preceding paragraphs, wherein the TEER value is greater than 2500 $\Omega \cdot cm^2$ at day four of culture.

[62] The device of any one of the preceding paragraphs, wherein the BMVECs are iPSC-derived and differentiated under low oxygen levels.

[63] A method of culturing cells, comprising: a) providing a microfluidic device comprising a membrane, the membrane comprising a top surface and a bottom surface; b) seeding cells on the bottom surface; and c) culturing the seeded cells under low oxygen conditions that support the maturation of brain microvascular endothelial cells (BMVECs).

[64] The method of any one of the preceding paragraphs, wherein the cells are selected from the group consisting of stem cells, cells differentiated from stem cells and primary cells.

[65] The method of any one of the preceding paragraphs, wherein the cells differentiated from stem cells are brain microvascular endothelial cells.

[66] The method of any one of the preceding paragraphs, the method further comprising seeding cells on the top surface and culturing the top surface seeded cells under conditions that support the maturation of at least one of astrocytes and neurons.

[67] The method of any one of the preceding paragraphs, wherein the BMVECs are GLUT-1+.

[68] The method of any one of the preceding paragraphs, wherein the low oxygen conditions comprise less than 10% oxygen.

[69] The method of any one of the preceding paragraphs, wherein the low oxygen conditions comprise approximately 5% oxygen.

[70] A method of generating brain microvascular endothelial cells, comprising the steps of: a) growing human stem cells on a surface; b) inducing differentiation of the cells by culturing the cells in unconditioned medium wherein endothelial cell (EC) regions of the cultures are observed; c) expanding the EC regions by culturing the cells in EC medium, the EC medium comprising retinoic acid (RA), so as to produce brain microvascular endothelial cells (BMVECs); d) seeding the BMVECs a microfluidic device having flow; and e) exposing the seeded cells to low oxygen conditions.

[71] The method of any one of the preceding paragraphs, wherein the seeding is done on a membrane in a microfluidic device, the membrane positioned in the device to encounter the flow of culture media, the flow causing the cells seeded on the membrane to experience shear forces.

[72] The method of any one of the preceding paragraphs, wherein the BMVECs are GLUT-1+.

[73] The method of any one of the preceding paragraphs, wherein the low oxygen conditions comprise less than 10% oxygen.

[74] The method of any one of the preceding paragraphs, wherein the low oxygen conditions comprise approximately 5% oxygen.

[75] The method of any one of the preceding paragraphs, wherein the exposing to low oxygen conditions of step e) is for approximately twenty-four hours, after which the oxygen levels are increased.

[76] The method of any one of the preceding paragraphs, wherein the surface comprises extracellular matrix proteins.

[77] The method of any one of the preceding paragraphs, further comprising the step of f) growing the cells to confluence.

[78] The method of any one of the preceding paragraphs, wherein the human stem cells are human pluripotent stem cells (hPSCs).

[79] The method of any one of the preceding paragraphs, wherein the human stem cells are induced pluripotent stem cells (iPSCs).

[80] The method of any one of the preceding paragraphs, the method further comprising g) co-culturing the BMVECs with a cell type selected from the group consisting of astrocytes, pericytes and differentiated neural progenitor cells (NPCs), so as to create a BBB model in vitro.

[81] A method of producing brain specific endothelial cells, comprising the steps of: a) growing human stem cells on a surface; b) inducing differentiation of the cells by culturing the cells in unconditioned medium wherein endothelial cell (EC) regions of the cultures are observed; c) exposing the cells to low oxygen conditions, and d) expanding the EC regions under the low oxygen conditions by culturing the cells in EC medium so as to produce brain microvascular endothelial cells (BMVECs).

[82] The method of any one of the preceding paragraphs, wherein the BMVECs are GLUT-1$^+$.

[83] The method of any one of the preceding paragraphs, wherein the low oxygen conditions comprise less than 10% oxygen.

[84] The method of any one of the preceding paragraphs, wherein the low oxygen conditions comprise approximately 5% oxygen.

[85] The method of any one of the preceding paragraphs, the method further comprising e) seeding the BMVECs on transwells or on a microfluidic device having flow.

[86] The method of any one of the preceding paragraphs, wherein the seeding is done on a membrane in a microfluidic device, the membrane positioned in the device to encounter the flow of culture media, the flow causing the cells seeded on the membrane to experience shear forces.

[87] The method of any one of the preceding paragraphs, the method further comprising f) exposing the seeded cells to low oxygen conditions.

[88] The method of any one of the preceding paragraphs, wherein the exposing to low oxygen conditions of step f) is for approximately twenty-four hours, after which the oxygen levels are increased.

[89] The method of any one of the preceding paragraphs, wherein the surface comprises extracellular matrix proteins.

[90] The method of any one of the preceding paragraphs, the further comprising the step of g) growing the cells to confluence.

[91] The method of any one of the preceding paragraphs, wherein the human stem cells are human pluripotent stem cells (hPSCs).

[92] The method of any one of the preceding paragraphs, wherein the human stem cells are induced pluripotent stem cells (iPSCs).

[93] A method of generating brain microvascular endothelial cells, comprising the steps of: a) growing human stem cells on a surface; b) inducing differentiation of the cells by culturing the cells in unconditioned medium wherein endothelial cell (EC) regions of the cultures are observed; c) exposing the cells to low oxygen conditions, and d) expanding the EC regions under the low oxygen conditions by culturing the cells in EC medium, the EC medium comprising retinoic acid (RA), so as to produce brain microvascular endothelial cells (BMVECs).

[94] The method of any one of the preceding paragraphs, wherein the BMVECs are GLUT-1+.

[95] The method of any one of the preceding paragraphs, wherein the low oxygen conditions comprise less than 10% oxygen.

[96] The method of any one of the preceding paragraphs, wherein the low oxygen conditions comprise approximately 5% oxygen.

[97] The method of any one of the preceding paragraphs, the method further comprising e) seeding the BMVECs on transwells or on a microfluidic device having flow.

[98] The method of any one of the preceding paragraphs, wherein the seeding is done on a membrane in a microfluidic device, the membrane positioned in the device to encounter the flow of culture media, the flow causing the cells seeded on the membrane to experience shear forces.

[99] The method of any one of the preceding paragraphs, further comprising f) exposing the seeded cells to low oxygen conditions.

[100] The method of any one of the preceding paragraphs, wherein the exposing to low oxygen conditions of step f) is for approximately twenty-four hours, after which the oxygen levels are increased.

[101] The method of any one of the preceding paragraphs, wherein the surface comprises extracellular matrix proteins.

[102] The method of any one of the preceding paragraphs, the method further comprising the step of g) growing the cells to confluence.

[103] The method of any one of the preceding paragraphs, wherein the human stem cells are human pluripotent stem cells (hPSCs).

[104] The method of any one of the preceding paragraphs, wherein the human stem cells are induced pluripotent stem cells (iPSCs).

[105] The method of any one of the preceding paragraphs, the method further comprising h) co-culturing the BMVECs with a cell type selected from the group consisting of astrocytes, pericytes and differentiated neural progenitor cells (NPCs), so as to create a BBB model in vitro.

[106] A method of generating brain microvascular endothelial cells, comprising the steps of: a) growing human stem cells on a surface; b) inducing differentiation of the cells by culturing the cells in unconditioned medium wherein endothelial cell (EC) regions of the cultures are observed; c) expanding the EC regions by culturing the cells in EC medium, the EC medium comprising retinoic acid (RA), so as to produce brain microvascular endothelial cells (BMVECs); d) seeding the BMVECs on transwells or on a microfluidic device having flow; and e) exposing the seeded cells to low oxygen conditions.

[107] The method of any one of the preceding paragraphs, wherein the seeding is done on a membrane in a microfluidic device, the membrane positioned in the device to encounter the flow of culture media, the flow causing the cells seeded on the membrane to experience shear forces.

[108] The method of any one of the preceding paragraphs, wherein the BMVECs are GLUT-1+.

[109] The method of any one of the preceding paragraphs, wherein the low oxygen conditions comprise less than 10% oxygen.

[110] The method of any one of the preceding paragraphs, wherein the low oxygen conditions comprise approximately 5% oxygen

[111] The method of any one of the preceding paragraphs, wherein the exposing to low oxygen conditions of step e) is for approximately twenty-four hours, after which the oxygen levels are increased.

[112] The method of any one of the preceding paragraphs, wherein the surface comprises extracellular matrix proteins.

[113] The method of any one of the preceding paragraphs, further comprising the step of f) growing the cells to confluence.

[114] The method of any one of the preceding paragraphs, wherein the human stem cells are human pluripotent stem cells (hPSCs).

[115] The method of any one of the preceding paragraphs, wherein the human stem cells are induced pluripotent stem cells (iPSCs).

[116] The method of any one of the preceding paragraphs, the method further comprising g) co-culturing the BMVECs with a cell type selected from the group consisting of astrocytes, pericytes and differentiated neural progenitor cells (NPCs), so as to create a BBB model in vitro.

This invention is further illustrated by the following example which should not be construed as limiting. The contents of all references cited throughout this application, as well as the figures and table are incorporated herein by reference.

Those skilled in the art will recognize, or be able to ascertain using not more than routine experimentation, many equivalents to the specific embodiments of the invention described herein. Such equivalents are intended to be encompassed by the following claims.

EXAMPLES

Materials and Methods
hPSC Culture and Differentiation

Human embryonic stem cells (hESCs) (H9)11 and induced pluripotent stem cells (iPS(IMR90)-413, iPS-DF19-9-11T35, and iPS-DF6-9-9T35) were maintained on irradiated mouse embryonic fibroblasts in standard unconditioned medium: Dulbecco's Modified Eagle's Medium/Ham's F12 containing 20% Knockout Serum Replacer (Invitrogen), 1×MEM nonessential amino acids (Invitrogen), 1 mM L-glutamine (Sigma), 0.1 mM β-mercaptoethanol (Sigma), and human basic fibroblast growth factor (bFGF, 4 ng/mL for hESCs and 100 ng/mL for iPSCs; Waisman Clinical Biomanufacturing Facility, University of Wisconsin-Madison). Prior to differentiation, cells were passaged onto Matrigel (BD Biosciences) in mTeSR1 medium (STEMCELL Technologies) (Ludwig, T. E. et al. Nature methods 3, 637-646 (2006)). After 8 days in mTeSR1 medium, the cells were switched to unconditioned medium lacking bFGF (referred to as UM throughout hereafter) to initiate differentiation. Major morphological changes were observed by day 5-7 of UM treatment, at which point the medium was switched to endothelial cell (EC) medium+retinoic acid (RA) (10 nM) human Endothelial Serum-Free Medium (Invitrogen) supplemented with 20 ng/mL bFGF and 1% platelet-poor plasma derived bovine serum (Biomedical Technologies, Inc.). Following 1-2 days of EC+RA medium treatment, cells were then cultured in EC medium until they reached confluence (typically 1-2 days).

hPSC-Derived BMVEC Co-Culture Experiments

For co-culture experiments, primary astrocytes were isolated as previously described (Weidenfeller, C., Svendsen, C. N. & Shusta, E. V. Journal of neurochemistry 101, 555-565 (2007). Briefly, cortices were isolated from P6 neonatal Sprague Dawley rats (Harlan) and minced in Hank's Balanced Salt Solution (HBSS; Sigma). This tissue was digested in HBSS containing 0.5 mg/mL trypsin (Mediatech, Inc.) in a 37° C. shaker bath for 25 min, followed by digestion in HBSS containing 114 U/mL DNase I (Worthington Biochemical) in a 37° C. shaker bath for 5 min. After trituration and filtration, cells were cultured on collagen-I-coated flasks (100 µg/mL; Sigma) in DMEM containing 10% qualified heat-inactivated fetal bovine serum (FBS; Invitrogen), 10% heat-inactivated horse serum (Sigma), 2 mM L-glutamine, and 1% antibiotic-antimycotic (Invitrogen). Human embryonic kidney 293 cells (HEK cells; ATCC) were cultured in DMEM supplemented with 10% FBS, 1 mM sodium pyruvate (Sigma), 2 g/L sodium bicarbonate (Fisher Scientific), 30 mM HEPES (Sigma), and 1% antibiotic-antimycotic, and used as a non-neural cell control. Co-culture of hPSC-derived BMVECs was initiated with primary rat astrocytes or pericytes or HEK cells in either EC medium or 70:30 (v/v) DMEM/F12 (Sigma/Invitrogen) supplemented with 1% antibiotic-antimycotic, 2% B27 (Invitrogen), and 10% FBS. Trans-endothelial electrical resistance (TEER) measurements were performed using an EVOM voltohmmeter (World Precision Instruments) at the start of co-culture and every 24 h thereafter. The resistance value ($\Omega \times cm^2$) of an empty filter coated with collagen/fibronectin was subtracted from each measurement. Permeability coefficients (Pe) were evaluated after 24 h of co-culture as previously described in Calabria, A. R. et al., Journal of neurochemistry 97, 922-933 (2006). For sodium fluorescein Pe measurements, 10% FBS medium containing 1 µM sodium fluorescein solution was added to the apical chamber of the TRANSWELL™ filter. 200 µL aliquots were extracted from the basolateral chamber (which contains 1.5 mL of medium) every 30 min and replaced by fresh medium. Using a fluorescent plate reader and calibration curve, the flux of fluorescein to the bottom chamber and permeability coefficients were calculated as described by Calabria et al supra.

Efflux Transport Assays

P-glycoprotein, BCRP, and MRP functionality were assessed using rhodamine 123 (Sigma), a preferred substrate for p-glycoprotein, and [14C]-doxorubicin (PerkinElmer), a substrate for all aforementioned efflux transporters. To assess activity, hPSC-derived BMVEC monolayers (absent astrocyte co-culture) were pre-incubated for 30 min on a rotator at 37° C. with or without 5 µM cyclosporin A (Sigma), 1 µM Ko143 (Sigma), or 10 µM MK 571 (Sigma), which are inhibitors of p-glycoprotein, BCRP, or various MRPs, respectively. BMVEC were then incubated with rhodamine 123 (10 µM) or doxorubicin (0.25 µCi) for 1 h on a rotator at 37° C. with or without inhibitors. Cells were then washed three times with ice-cold PBS and lysed with 5% Triton X-100 (TX-100; Fisher). Fluorescence (485 nm excitation and 530 nm emission) was measured using a plate reader and normalized to cell counts obtained using a hemocytometer, while radioactivity was measured using a liquid scintillation counter. To quantify apical-to-basolateral transport, hPSC-derived BMVEC monolayers on TRANSWELL™ filters were co-cultured with astrocytes for 24 h and then pre-incubated with or without inhibitors in their original co-culture medium containing 10% FBS for 60 min, followed by addition of rhodamine 123 or doxorubicin to the upper chamber. After another 60 min, aliquots were extracted from the bottom chamber and transport was quantified on a plate reader or scintillation counter. To quantify basolateral-to-apical transport, hPSC-derived BMVEC monolayers on TRANSWELL™ filters were pre-incubated with or without cyclosporin A in co-culture medium containing 10% FBS for 60 min, followed by addition of rhodamine 123 to the lower chamber. After 3 h, aliquots were extracted from the upper chamber and fluorescence quantified on a plate reader. All measurements of accumulation and transport were normalized to accumulation and transport in the absence of inhibitor. Rhodamine accumulation or transport studies were carried out in fresh co-culture medium containing 10% FBS, while doxorubicin studies were conducted in transport buffer (described above). Sucrose permeability and TEER measurements were used to confirm monolayer integrity in the presence of inhibitors.

Reverse-Transcription Polymerase Chain Reaction (RT-PCR), Quantitative RT-PCR, and Gel Electrophoresis Cells were differentiated as previously described. For RNA collection, cells were washed once with PBS and dissociated with trypsin or accutase. Total RNA was extracted using an RNeasy Mini Kit (Qiagen) according to the manufacturer's instructions. cDNA was generated from 1 µg of RNA using Omniscript reverse transcriptase (Qiagen) and oligo-dT primers (Invitrogen). Quantitative PCR (qPCR) was then performed using 1 µL of cDNA and iQ SYBR Green Supermix (Bio-Rad) on an iCycler (Bio-Rad). RT-PCR was also performed using GoTaq Green Master Mix (Promega). Primer sequences are supplied in Table 8. Relative expression was quantified using the comparative cycle threshold (CT) method, normalizing to glyceraldehyde-3-phosphate dehydrogenase (GAPDH) expression. Fold difference was calculated as $X-\Delta\Delta CT$, where x refers to primer efficiency calculated according LinRegPCR version 12.359. Transcript amplification was analyzed by 2% agarose gel electrophoresis of the qPCR or RT-PCR products.

Measurement of BMVEC Properties

Co-culture of iPSC-derived BMVECs was initiated with primary rat astrocytes or human embryonic kidney 293 cells or pericytes in either EC media (defined above) or 70:30 (v/v) DMEM/F12 (Sigma/Invitrogen) supplemented with 1% (v/v) antibiotic-antimycotic, 2% (v/v) B27, and 10% (v/v) FBS. Transendothelial electrical resistance measurements were performed using an EVOM voltohmmeter (World Precision Instruments, Sarasota, Fla., USA) at the start of co-culture and approximately every 24 hours thereafter. The resistance value (ohms×cm2) of an empty filter coated with collagen/fibronectin was subtracted from each measurement. Permeability coefficients were evaluated after 24 hours of co-culture as previously described. Briefly, a solution of 1 µM sodium fluorescene was added to the apical chamber of the TRANSWELL™ filter and 200 µL aliquots were extracted from the basolateral chamber every 30 minutes. Using a fluorescent plate reader and calibration curve, the rate of fluorescene influx to the bottom chamber was calculated, and final values for permeability coefficients were then calculated according to Calabria et al.

To assess p-glycoprotein functionality, standard rhodamine 123 (Sigma) efflux assays were employed. For the rhodamine 123 accumulation assay, confluent IMR90-derived monolayers were pre-incubated with or without 5 µM cyclosporin A (Sigma) at 37° C. for 30 minutes with shaking. 10 µM rhodamine 123 was then added with or without inhibitor and the cells were incubated at 37° C. for 60 minutes with shaking. Cells were then washed three times with ice-cold PBS and lysed with 5% TX-100. Fluorescence was measured using the plate reader. Separate wells of cells incubated with or without inhibitor were trypsinized and counted with a hemocytometer to normalize the fluorescent readings to cell number. For the apical-to-basolateral transport study, the cells were pre-incubated with or without 5 µM cyclosporin A for 60 minutes, followed by addition of 10 µM rhodamine 123 to the upper chamber. After another 60 minutes, aliquots were extracted from the bottom chamber and analyzed on the plate reader. For the basolateral-to-apical transport study, the cells were pre-incubated with or without 5 µM cyclosporin A for 60 minutes, followed by addition of 10 µM rhodamine 123 to the lower chamber. After 3 hours, aliquots were extracted from the upper chamber and analyzed on the plate reader. All samples were normalized to the non-inhibitor values. All TEER, permeability, and efflux assay experiments were performed with triplicate filters or wells from which the reported averages and standard deviations are calculated.

Example 1

Protocols as described in U.S. Patent Application Publication Nos. 20120015395 and 20140127800, hereby incorporated by reference, were modified. IMR90-4 iPSC were seeded on 6-wells culture dishes at Day minus eleven (D-11) (see FIG. 1), and mTesR1 media was switched to differentiation media (UM from D-8 to D2; EC+retinoic acid (RA) from D-2 to D1) to induce differentiation into brain vascular endothelial cells. At D0, differentiated brain vascular endothelial cell were seeded on transwells or polydimethylsiloxane (PDMS) microfluidic chips. At D1, retinoic acid (RA), and basic growth factor (bFGF) were deprived from EC media to induce maturation of brain vascular endothelial cells. The oxygen tension during iPSC differentiation was controlled as follows:

Hypoxia Protocol 1: Four hours after seeding brain vascular endothelial cells on transwells or PDMS microfluidic chips (D0), the cells were exposed to hypoxia (5% $O_2$, balanced with $N_2$) for 24 h in an incubator. At D1, the cells were returned to normoxic conditions (20% $O_2$) and cultured.

Hypoxia Protocol 2: From D–8 after switching to UM media (unconditioned media), cells were exposed to hypoxia (5% $O_2$, balanced with $N_2$) for 10 days in an incubator. Four hours after seeding iPSC-derived brain vascular endothelial cells (BMVEC) on transwells or PDMS chip at D0, cells were again exposed to hypoxia (5% $O_2$, balanced with $N_2$) for 24 h in an incubator. At D1, the cells were returned to normoxic condition (20% $O_2$) and cultured.

To allow for improved BBB function, iPSC-derived BMVEC can be co-cultured with primary or stem cells derived pericytes, astrocytes and neural precursor cells or neurons.

Example 2

Figure 2B:
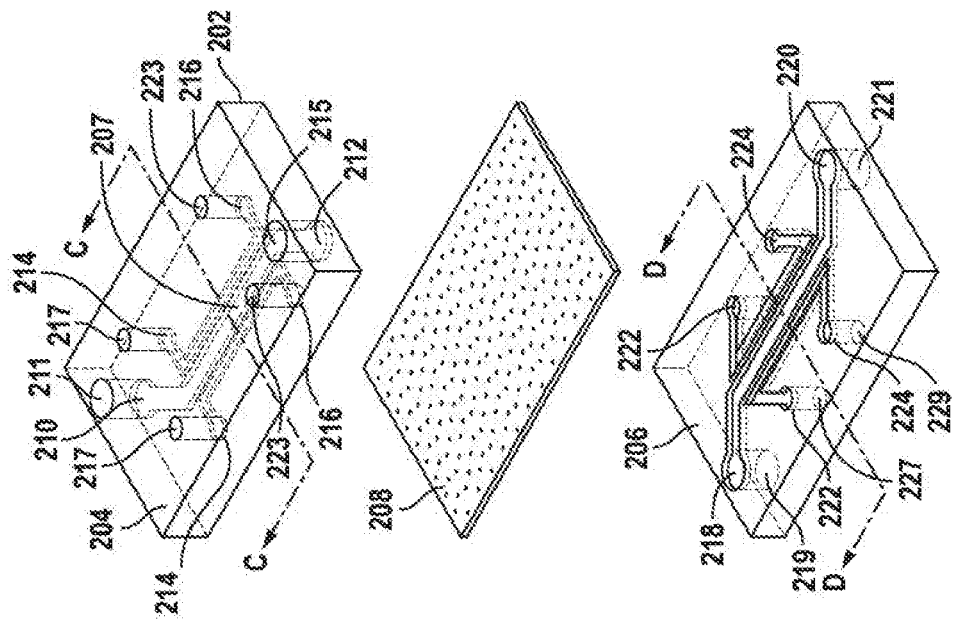
FIG. 2B illustrates an exploded view of the organ mimic device in accordance with an embodiment showing the membrane 208 having a top and bottom surfaces, upon which the described cells can be cultured.
Figure 2A:
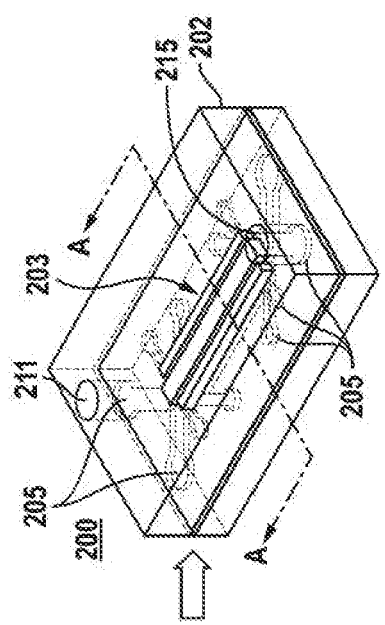
FIG. 2A illustrates a perspective view of one embodiment of a microfluidic "organ mimic" device that can be used for cell seeding as taught herein.

FIG. 2A illustrates a perspective view of the tissue interface microfluidic device in accordance with an embodiment. In particular, as shown in FIG. 2A, the microfluidic device 200 preferably includes a body 202 having a branched microchannel design 203 in accordance with an embodiment. The body 202 may be made of a flexible material, although it is contemplated that the body be alternatively made of a non-flexible material. It should be noted that the microchannel design 203 is only exemplary and not limited to the configuration shown in FIG. 2A. The body 202 is preferably made of a flexible biocompatible polymer, including but not limited to, polydimethyl siloxane (PDMS), or polyimide.

The device in FIG. 2A includes a plurality of ports 205 which will be described in more detail below. In addition, the branched configuration 203 includes a tissue-tissue interface simulation region (membrane 208 in FIG. 2B having a top 208A and bottom 208B surface) where cell behavior and/or passage of gases, chemicals, molecules, particulates and cells are monitored. FIG. 2B illustrates an exploded view of the organ mimic device in accordance with an embodiment. In particular, the outer body 202 of the device 200 is preferably comprised of a first outer body portion 204, a second outer body portion 206 and an intermediary porous membrane 208 conFIG.d to be mounted between the first and second outer body portions 204, 206 when the portions 204, 206 are mounted to one another to form the overall body.

FIG. 2B illustrates an exploded view of the device in accordance with an embodiment. As shown in FIG. 2B, the first outer body portion 204 includes one or more inlet fluid ports 210 preferably in communication with one or more corresponding inlet apertures 211 located on an outer surface of the body 202. The microfluidic device is preferably connected to a fluid source (not shown) via the inlet aperture 211 in which fluid travels from the fluid source into the device through the inlet fluid port 210.

Additionally, the first outer body portion 204 includes one or more outlet fluid ports 212 preferably in communication with one or more corresponding outlet apertures 215 on the outer surface of the body 202. It should be noted that the device 200 may be set up such that the fluid port 210 is an outlet and fluid port 212 is an inlet. Although the inlet and outlet apertures 211, 215 are shown on the top surface of the body 202, one or more of the apertures may be located on one or more sides of the body.

Example 3

Figure 3:
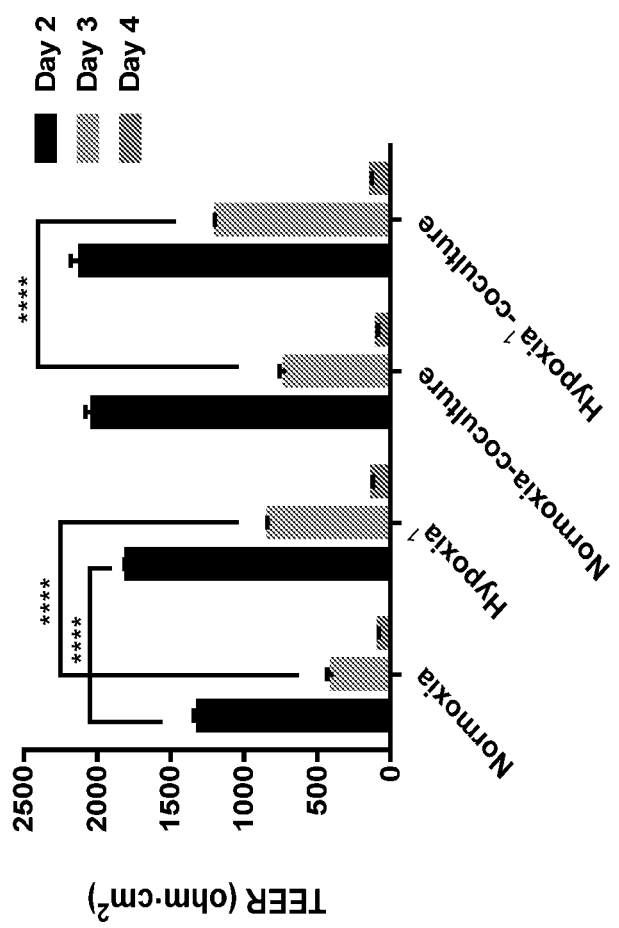
FIG. 3 is a bar graph showing transepithelial electric resistance (TEER) values of iPSC-derived BMVEC differentiated in normoxia and hypoxia 1 conditions. Co-culture; non-contact co-culture of BMVEC with astrocyte and pericyte from day zero (D0). Data were analyzed with two-way analysis of variance (ANOVA) with Tukey test; *$P<0.05$, $P<0.01$, *$P<0.001$, ****$P<0.0001$.
Figure 5A:
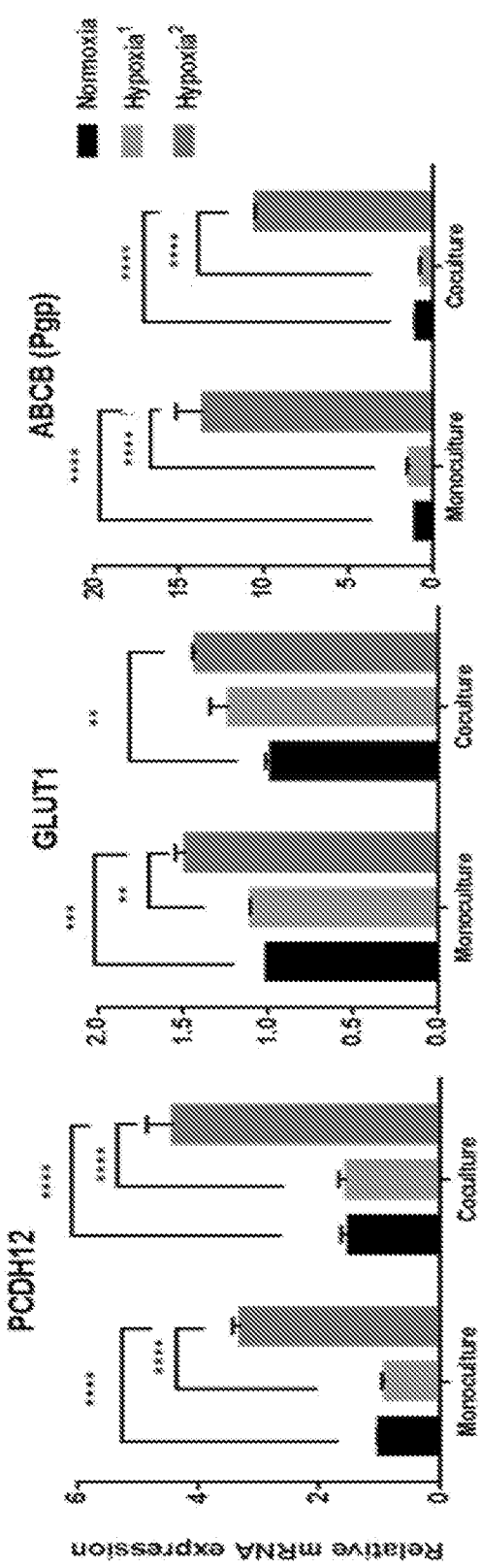
Figure 5B:
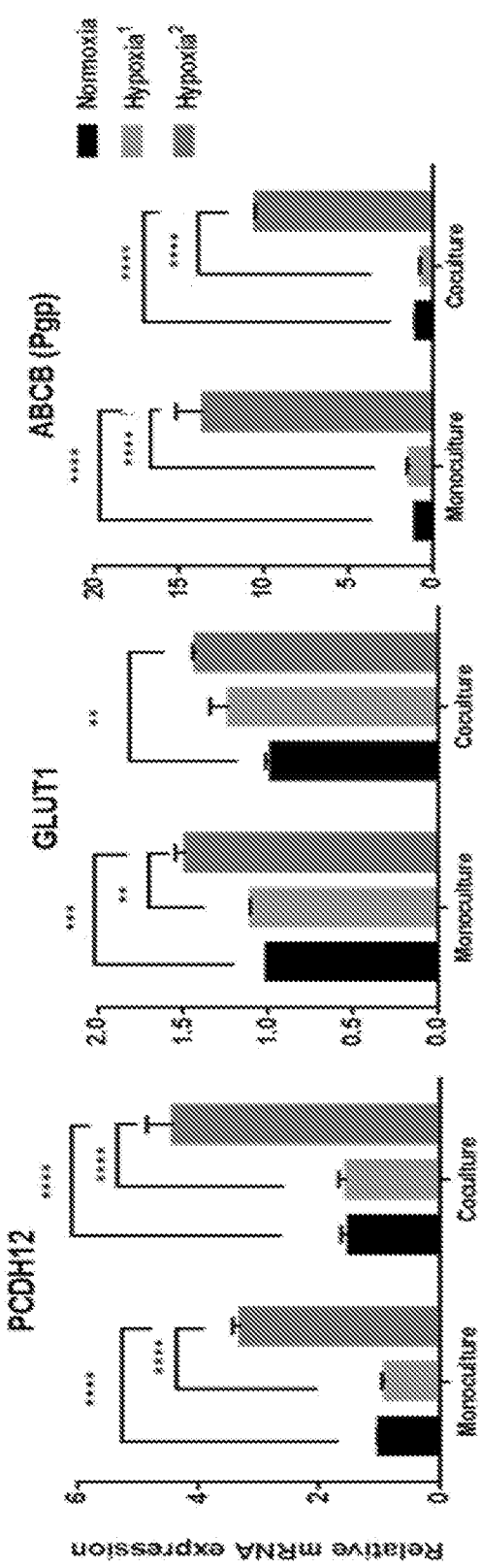
Figure 5C:
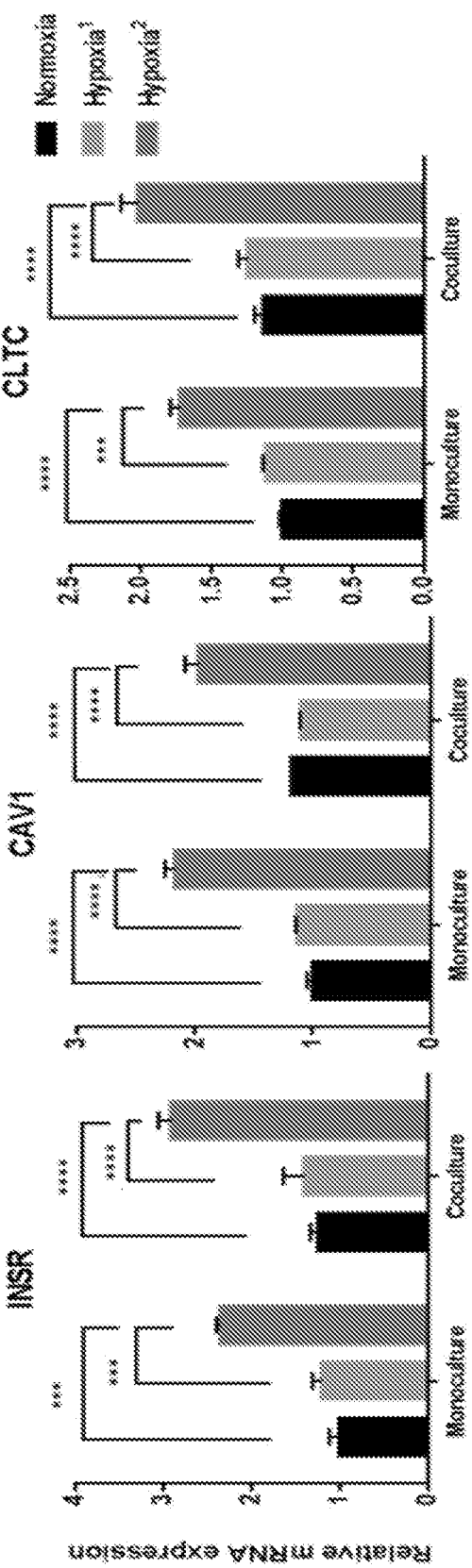
Figure 5D:
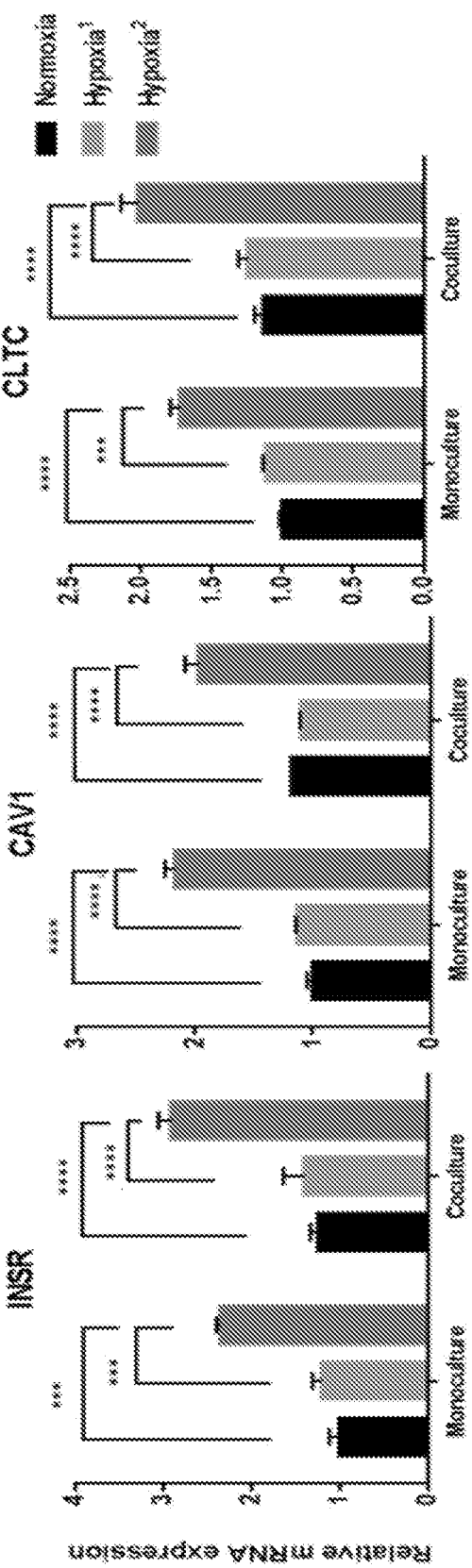
Figure 5E:
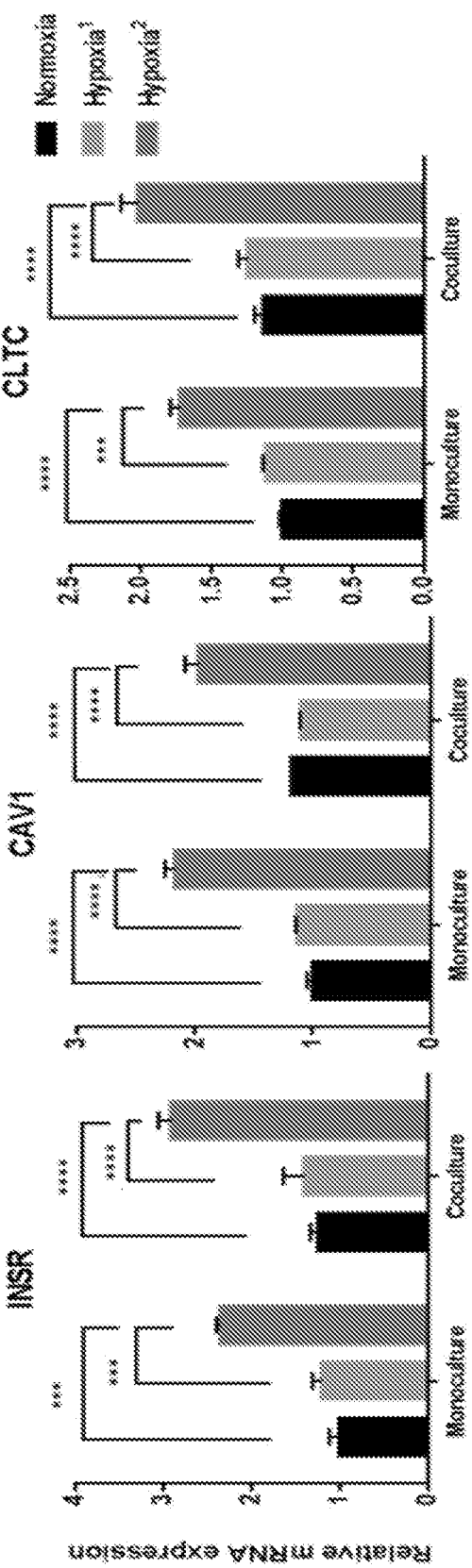
Figure 5F:
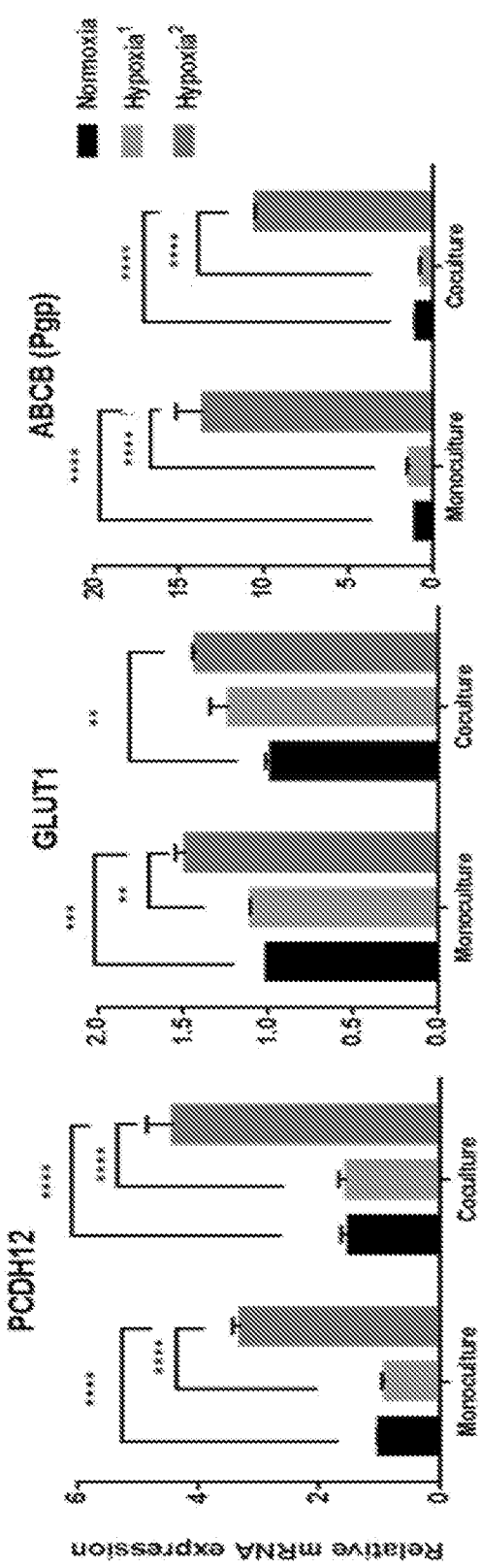

A hallmark of the BBB is the high TEER—a consequence of the tight junction protein interactions between adjacent brain endothelial cells. As shown in FIG. 3, compared to BMVEC differentiated in normoxia as in previous published protocols, BMVEC cultured under hypoxia protocol 1 conditions (FIG. 1) demonstrated significantly higher TEER values at D2 and D3. Co-culture with astrocytes and pericytes (glial cells) also significantly increased the barrier function of BMVEC. Although hypoxia protocol 1 conditions helped to increase barrier function of BMVEC, stable levels of high TEER were not maintained.

The investigators prolonged the duration of hypoxia exposure in BMVEC differentiation from iPSC using hypoxia protocol 2. At D3 and D4, TEER value of BMVEC cultured in hypoxia protocol 2 conditions reached to 2427 $\Omega \cdot cm^2$ and 2233 $\Omega \cdot cm^2$, respectively, while those of normoxia and hypoxia protocol 1 conditions decreased to below 300 $\Omega \cdot cm^2$ (FIG. 4A) at D3. Co-culture with primary astrocytes and pericytes improved maintenance of consistent high levels of TEER (FIG. 4B). TEER value of BMVEC cultured in hypoxia protocol 2 gradually increased and reached to 2900 $\Omega \cdot cm^2$ at D4 during co-culture conditions (FIG. 4B). These results indicate that exposure of iPSC to physiologically relevant hypoxia conditions followed by re-oxygenation and co-culture with glial cells generate BMVECs with a more stable and higher barrier function.

Example 4

The investigators analyzed the mRNA expressions of iPSC-derived BMVECs indicating characteristic BBB properties. Exposure of iPSC to hypoxial and hypoxia 2 conditions did not affect the expression of TJP1 (ZO-1; tight junction protein), OCLN (occludin; tight junction protein), TFR1 (transferrin receptor), and CD31 (Platelet endothelial cell adhesion molecule; endothelial cell intercellular junctions) (data not shown). iPSC differentiation under hypoxia 2 conditions significantly increased the expressions of PCDH12 (VE-cad; integral membrane protein, adherens junctions), ABCB (Pgp; transmembrane efflux pump), INSR (Insulin receptor), GLUT1 (glucose transporter 1), CAV1 (caveolin-1; caveolae protein), CLTC (clathrin heavy chain 1; clathrin vesicle protein), ABCC4 (MRP4; multiple drug resistance-associated protein 4), ABCC1 (MRP1; multiple drug resistance-associated protein 1), and BCRP (breast cancer resistance protein) as shown in FIGS. 5A-5I. The increase of VE-cad (FIG. 5A) in BMVECs (hypoxia 2) contributed to improvement of barrier function and higher level of GLUT1 (FIG. 5B) expression is likely to improve the maintenance of brain endothelium integrity. Significantly increased expression of genes related to transcytotic drug delivery and metabolism including ABCB (FIG. 5C), INSR (FIG. 5D), CAV1 (FIG. 5E), CLTC (FIG. 5F), ABCC4 (FIG. 5G), ABCC1 (FIG. 5H), and BCRP (FIG. 5I) indicate the potential of iPSC-derived BMVECs under hypoxia 2 condition as a promising in vitro model to test drugs targeting the central nervous system. These data demonstrate that the novel method of physiologically relevant hypoxia treatment improved the BBB attributes of iPSC-derived BMVECs.

Potential application of the method: efflux transporters (e.g. ABCB, ABCC4, ABCC1, and BCRP)-mediated drug interactions are an emerging field with limited experience in translating in vitro findings to the clinic. For example, iPS-derived BMVEC generated using published protocol has shown lower efflux ratio (1.3-fold) of Doxorubicin (efflux substrate) (Sci Rep, 2014, 4) compared to in vivo efflux ratios (2.4-fold) (Cell, 1994, 77, 4), implying that ABCB (P-gp) activity in vitro was not able to recapitulate the drug interaction in vivo. By contrast, iPS-derived BMVEC generated under controlled oxygen tension has shown significantly increased efflux transporters (FIGS. 5C, 5G, 5H, and 5I), which indicates the improved in vitro BBB model to test efflux substrates. Substrates of efflux transporters that are expressed in the brain include numerous anticancer drugs (e.g. doxorubicin, docetaxel, and paclitaxel), analgesics (morphine), antiepileptic drugs (felbamate), and anti-HIV drugs (AZT, and PMEA). By inhibiting efflux transporters of iPS-derived BMVEC using inhibitors or siRNA, distribution and interactions of efflux substrates can be tested at a physiologically relevant level. Furthermore, reliable investigation of modulation of efflux transporter to enhance the distribution of drug can be conducted on cellular level.

Example 5

Figure 6:
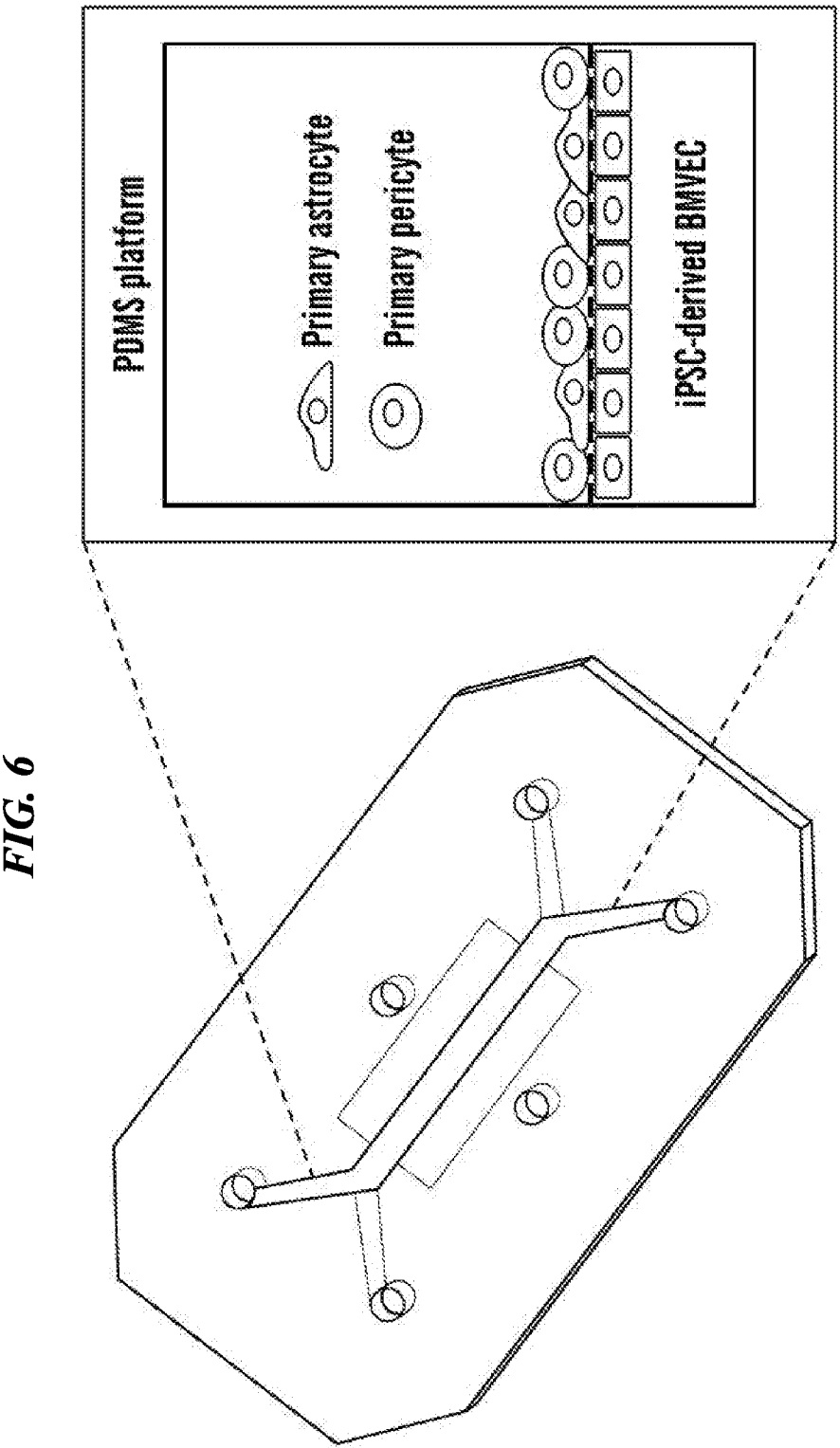
FIG. 6 shows the schematic representation of a microfluidic device with a membrane and cultured cells therein on the membrane.

An example of how to generate the iPSC-derived, hypoxia differentiated BBB-on-a-chip using microfluidic device is given in FIG. 6A. The basic device contains two microchannels, separated by a porous membrane. The top and bottom channels have a width of 1 micrometer (μm), height of 200 mm and a length of 2 cm. The two channels are separated by a 2 μm pore sized polyethylene terephthalate membrane. The human iPSC-derived, hypoxia differentiated brain endothelial cells were cultured on the top channel, and mixture of primary astrocyte and pericyte was seeded on the membrane of bottom channel (data not shown). Human iPSC (IMR-90-4) were induced to differentiate into brain endothelial cells according to the method of E. Shusta (Nat biotechnol, 2012, 30, 8) with modification of controlling oxygen level as per physiologically relevant oxygen tension to improve BBB attributes of iPSC-derived brain endothelial cells. The iPSC-derived BMVECs on a BBB chip were exposed to physiological shear stress (6 dyne/cm2) for 24 h and evaluated. The tight junctions and the membrane-bound GLUT1 transporter of the BMVECs remain intact under this physiological shear stress (data not shown).

Example 6

Figure 7:
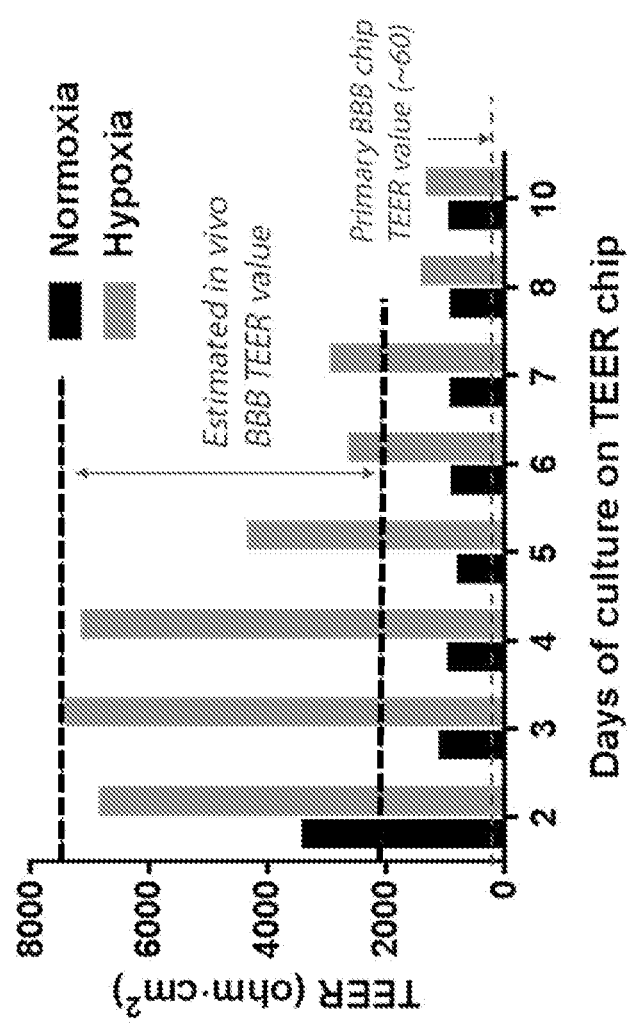
FIG. 7 shows bar graphs of representative TEER values of the BBB measured in situ in an organ chip microsystem developed at the Wyss Institute. The BMVECs in the chip were cultured and differentiated under the hypoxia 2 conditions as shown in FIG. 1.

The presently described iPSC-derived, hypoxia differentiated BMVECs demonstrated to have an enhanced physical barrier function in the BBB Chip. iPSC-derived BMVECs were cultured and differentiated as previously described and placed in a microfluidic device to give a BBB model chip. The TEER values of iPSC-derived BBB chip having normoxia cultured iPSC-derived brain endothelial cells had shown huge decrease of TEER value from day 3. On the other hand, iPSC-derived brain endothelial cells cultured under the described hypoxia 2 conditions produced a more stable maintenance of physiological physical barrier function of BBB chip for a week (FIG. 7).

Example 7

Figure 8B:
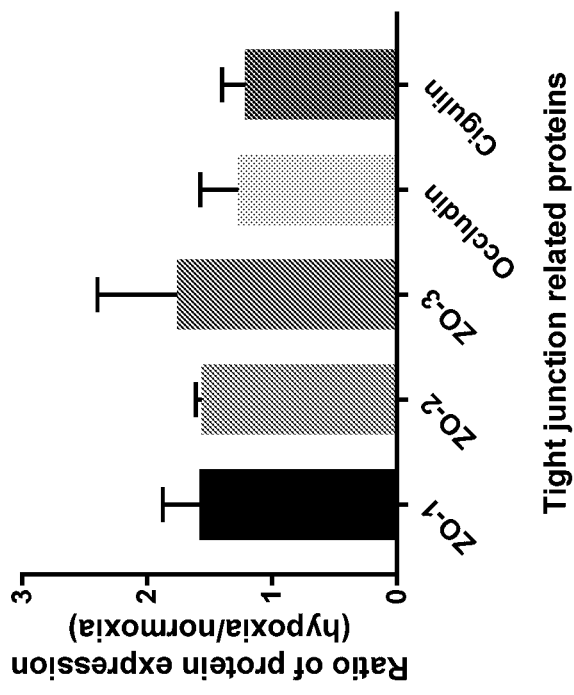
FIG. 8A-8B show bar graphs of the proteomics analysis of BBB function related protein expressions under hypoxia and normoxia condition. The ratio of protein expression of hypoxia stimulated iPSC-derived BMVEC to normoxia control. The BMVECs forming the BBB were cultured and differentiated under the hypoxia 2 conditions as shown in FIG. 1.
Figure 8A:
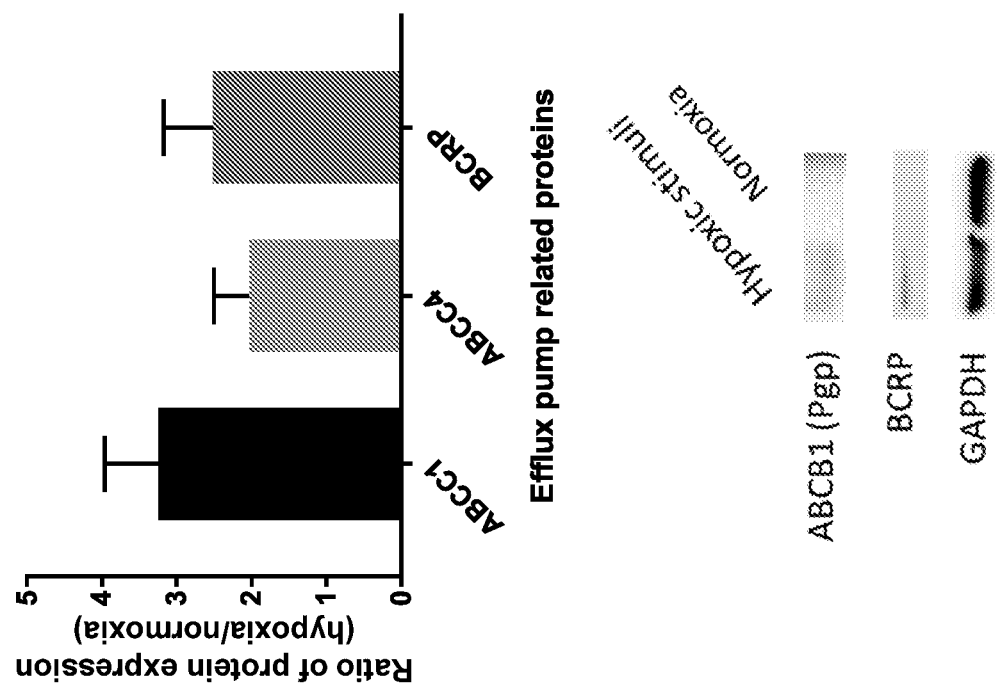

The presently described iPSC-derived, hypoxia differentiated BMVECs also demonstrated to have an improved BBB function related protein expression. The investigators tested the protein expression of proteins related to efflux as well as proteins related to the formation of tight junctions. (FIGS. 8A-B). For iPSC differentiation under hypoxia condition, there were significant increase in the expressions of efflux pump proteins—ABCC1, ABCC4, and BCRP. Western blot detection of ABCB1 and BCRP also clearly showed that hypoxia stimuli increased the efflux pump proteins. (FIG. 8A). Similarly, there were significant increases in tight junction function related proteins—ZO-1, ZO-2, ZO-3, Occludin, and Cigulin in hypoxia stimulated iPSC-derived BMVECs. (FIG. 8B).

Example 8

The presently described iPSC-derived, hypoxia differentiated BMVECs also demonstrated to have an improved BBB efflux pump systems.

The function of efflux pump of in vitro BBB model is important for testing brain drug as a metabolic barrier because many hydrophobic brain drug cannot reach to central nervous system due to efflux pump. However, lack of human BBB model having physiologically relevant metabolic barrier function limited the brain drug in vitro test. Here, the investigators created a microfluidic chip that models the human blood brain barrier (BBB) for testing the efficacies of the efflux pumps in the barrier. The BBB model chip comprises iPSC-derived, hypoxia-stimulated or -differentiated BMVECs.

Figures 9A, 9B:
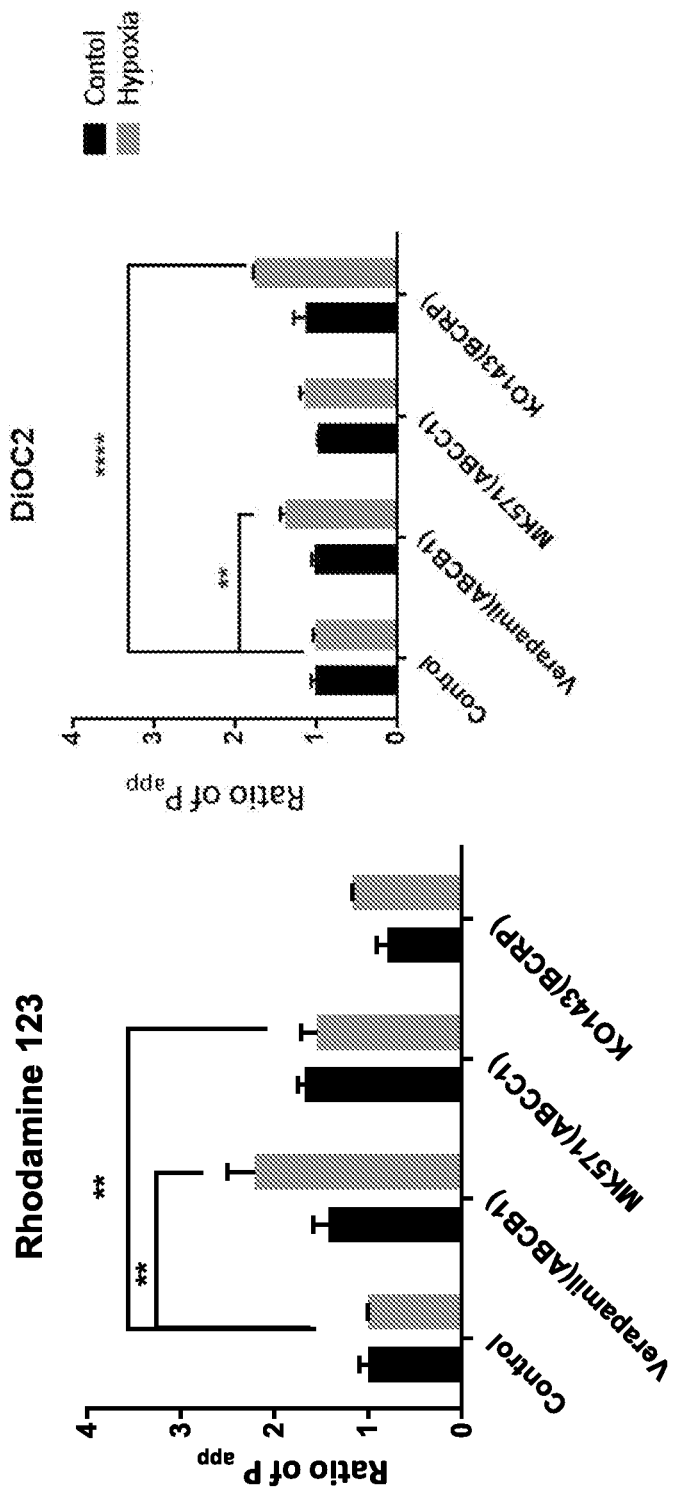
FIGS. 9A-9C are bar graphs showing the inhibition of the efflux transporter in control and hypoxic stimulated BBB chips by verapamil, MK-571 or KO143. Apparent permeability ($P_{app}$ cm/s) is measured by the permeability of rhodamine 123 (in FIG. 9A), DiOC2 (in FIG. 9B), and doxorubicin (FIG. 9C). All inhibitor-treated samples were independently normalized to the corresponding mock control. The information of each inhibitor and each efflux system pumping Rhodamine 123 and DiOC2 are shown in the insert Table in FIG. 9C.

Blockage of ABCB1 or ABCC1 of hypoxia-stimulated BBB Chip with metabolic inhibitors significantly increased the Papp of Rhodamine 123 (FIG. 9A), while normoxia control BBB chip did not show any change of Rhodamine 123 penetration, which implies that hypoxia stimuli enhances the efflux pump and substrate selectivity. DiO2 test also has shown enhanced efflux pump function by hypoxia stimulation (FIG. 9B). Hypoxia-stimulated BBB chip means hypoxic stimulated BMVEC are cultured on the chip.

Figure 9C:
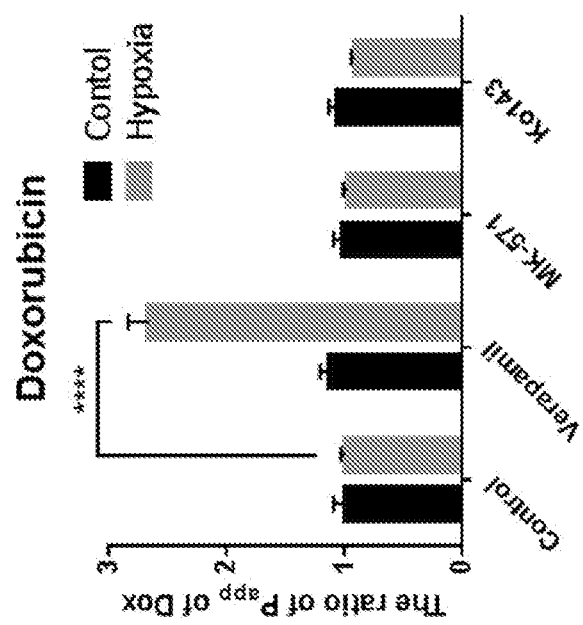

Doxorubicin is known as a substrate of ABCB1. While normoxia control BBB chip did not show significant change of doxorubicin BBB penetration by verapamil (ABCB1 inhibitor) treatment on hypoxia BBB chip showed 2.7-fold higher doxorubicin permeability, which repeats the in vivo doxorubicin studies (FIG. 9C).

Example 9

Hypoxia-induced factor 1 (HIF1) is involved in the mechanism for forming improved BBB in vitro.

To confirm that HIF1alpha (HIF1-α) expression is increased in hypoxia condition, total RNA was extracted from iPSCs that had been undergoing differentiation in hypoxia conditions for one day, and the HIF1-α mRNA expression was analyzed using qRT-PCR.

To demonstrate that HIF1 alpha is involved in the mechanism, 100 nM or 200 nM of dimethyloxaloylglycine (DMOG), was added to the iPSC undergoing differentiation in normoxia condition. DMOG is an inhibitor of prolyl hydroxylase (PHD) and the asparaginyl hydroxylase factor inhibiting HIF (FIH). DMOG has been observed to upregulate hypoxia inducible factor-1α (HIF-1α) in cells. Addition of DMOG to differentiating iPSCs in normoxia conditions would upregulate the HIF-1α in the differentiating iPSCs.

The TEER values of BBB models on chip, formed with BMVEC differentiated under normoxia, in presence of DMOG under normoxia, or hypoxia, were measured and compared.

Figure 10A:
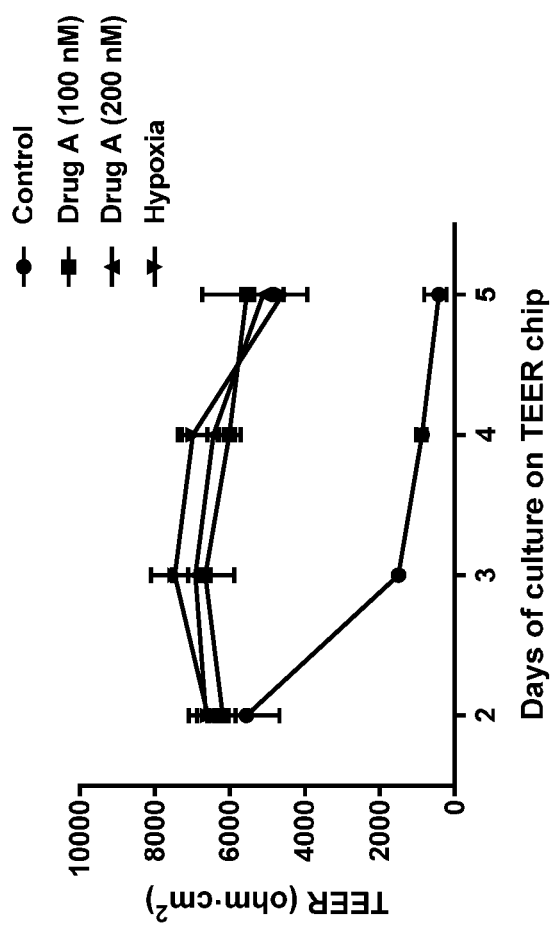
FIG. 10A are bar graphs showing a 10-fold increase in HIF1alpha (HIF1a) expression in hypoxia stimulated iPSC under differentiation for one day (D−1).
Figure 10B:
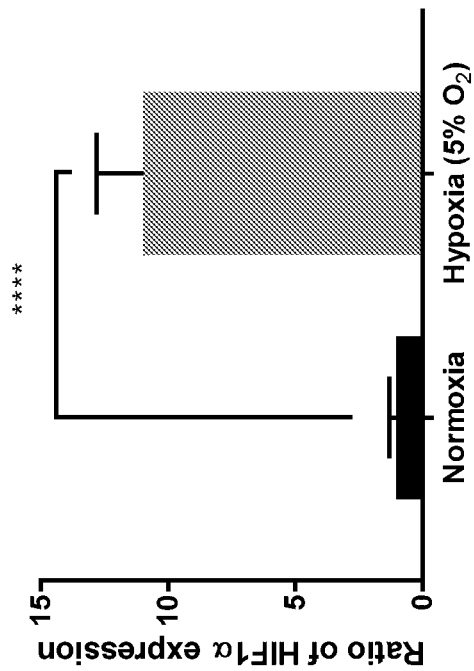
FIG. 10B shows that dimethyloxaloylglycine (DMOG), an inhibitor of prolyl hydroxylase (PHD) and the asparaginyl hydroxylase factor inhibiting HIF increases the accumulation of HIF1 was treated to iPSC under differentiation.

HIF1 is one of the main cellular responses to hypoxia that operates in numerous cell type. FIG. 10A shows that HIF1-α expression was increased about 10-fold in hypoxia-stimulated iPSC under differentiation by Day one (D−1). Considering BBB formation occurs under hypoxia condition, HIF1 is essential for embryo vascular development. To demonstrate that HIF1 is involved in the improved BBB formed in vitro under hypoxic conditions, the HIF1-α expression in normoxia iPSC-derived BMVECs was upregulated with, DMOG. Treatment with DMOG (Drug A in FIG. 10B) at both concentrations of 100 nM or 200 nM of the normoxia iPSC-derived BMVECs produced BBB that were similar to the BBB formed with hypoxia iPSC-derived BMVECs.

What is claimed is:

1. A method of generating brain microvascular endothelial cells, comprising:
    a) growing induced pluripotent stem cells (iPSCs) on a surface;
    b) inducing differentiation of said stem cells by culturing said stem cells with unconditioned medium lacking bFGF under low oxygen conditions to produce endothelial cell (EC) regions of the cell culture;
    c) expanding said EC regions by culturing the cells in medium comprising retinoic acid so as produce brain microvascular endothelial cells (BMVECs);
    d) seeding said BMVECs on a microfluidic device having flow;
    e) exposing said seeded BMVECs to low oxygen conditions for at least 24 hours;
    f) returning said BMVECs to normal oxygen tension; and
    g) culturing said BMVECs such that said BMVECs have increased expression of the glucose transporter protein GLUT1 as compared to BMVECs cultured under normal oxygen conditions.

2. The method of claim 1, wherein said low oxygen conditions of step b) and e) comprise 5% $O_2$ balanced with $N_2$.

3. The method of claim 1, wherein said BMVECs are co-cultured in step g) with astrocytes and pericytes.

4. A method of generating brain microvascular endothelial cells, comprising:
    a) growing induced pluripotent stem cells (iPSCs) on a surface;
    b) inducing differentiation of said stem cells by culturing said stem cells with unconditioned medium lacking bFGF under low oxygen conditions to produce endothelial cell (EC) regions of the cell culture;
    c) expanding said EC regions by culturing the cells in medium comprising retinoic acid so as produce brain microvascular endothelial cells (BMVECs);
    d) seeding said BMVECs on a microfluidic device having flow;
    e) exposing said seeded BMVECs to low oxygen conditions for at least 24 hours;
    f) returning said BMVECs to normal oxygen tension; and
    g) culturing said BMVECs such that said BMVECs have increased expression of the insulin receptor protein INSR as compared to normal oxygen conditions.

5. The method of claim 4, wherein said increased expression of said insulin receptor protein INSR is approximately two-fold.

6. The method of claim 4, wherein said increased expression of said insulin transporter protein INSR is approximately three-fold.

7. The method of claim 4, wherein said low oxygen conditions of step b) and e) comprise 5% $O_2$ balanced with $N_2$.

8. The method of claim 4, wherein said BMVECs are co-cultured in step g) with astrocytes and pericytes.

9. A method of generating brain microvascular endothelial cells, comprising:
    a) growing induced pluripotent stem cells (iPSCs) on a surface;
    b) inducing differentiation of said stem cells by culturing said stem cells with unconditioned medium lacking bFGF under low oxygen conditions to produce endothelial cell (EC) regions of the culture;
    c) expanding said EC regions by culturing the cells in medium comprising retinoic acid, so as to produce brain microvascular endothelial cells (BMVECs);
    d) seeding said BMVECs on a microfluidic device having flow;
    e) exposing said seeded BMVECs to low oxygen conditions for at least 24 hours;
    f) returning said BMVECs to normal oxygen tension; and
    g) culturing said BMVECs such that said BMVECs have increased expression of caveolin-1 protein as compared to normal oxygen conditions.

10. The method of claim 9, wherein said increased expression of said caveolin-1 protein is approximately two-fold.

11. The method of claim 9, wherein said low oxygen conditions of step b) and e) comprise 5% $O_2$ balanced with $N_2$.

12. The method of claim 9, wherein said BMVECs are co-cultured in step g) with astrocytes and pericytes.

13. A method of generating brain microvascular endothelial cells, comprising:
    a) growing induced pluripotent stem cells (iPSCs) on a surface;
    b) inducing differentiation of said stem cells by culturing said stem cells with unconditioned medium lacking bFGF under low oxygen conditions to produce endothelial cell (EC) regions of the culture;
    c) expanding said EC regions by culturing the cells in medium comprising retinoic acid, so as to produce brain microvascular endothelial cells (BMVECs);
    d) seeding said BMVECs on a microfluidic device having flow;
    e) exposing said seeded BMVECs to low oxygen conditions for at least 24 hours;
    f) returning said BMVECs to normal oxygen tension; and
    g) culturing said BMVECs such that said BMVECs have increased expression of the clathrin heavy chain 1 protein CLTC as compared to normal oxygen conditions.

14. The method of claim 13, wherein said increased expression of said clathrin heavy chain 1 protein CLTC is approximately two-fold.

15. The method of claim 13, wherein said low oxygen conditions of step b) and e) comprise 5% $O_2$ balanced with $N_2$.

16. The method of claim 13, wherein said BMVECs are co-cultured in step g) with astrocytes and pericytes.

17. A method of generating brain microvascular endothelial cells, comprising:
    a) growing induced pluripotent stem cells (iPSCs) on a surface;

b) inducing differentiation of said stem cells by culturing said stem cells with unconditioned medium lacking bFGF under low oxygen conditions to produce endothelial cell (EC) regions of the culture;

c) expanding said EC regions by culturing the cells in medium comprising retinoic acid, so as to produce brain microvascular endothelial cells (BMVECs);

d) seeding said BMVECs on a microfluidic device having flow;

e) exposing said seeded BMVECs to low oxygen conditions for at least 24 hours;

f) returning said BMVECs to normal oxygen tension; and g) culturing said BMVECs such that said BMVECs have increased expression of the multi drug resistance protein ABCC4, ABCC1, or BCRP as compared to normal oxygen conditions.

18. The method of claim 17, wherein said increased expression of said ABCC4 or ABCC1 is approximately two-fold.

19. The method of claim 17, wherein said increased expression of said BCRP is approximately twenty-two fold.

20. The method of claim 17, wherein said low oxygen conditions of step b) and e) comprise 5% $O_2$ balanced with $N_2$.

21. The method of claim 17, wherein said BMVECs are co-cultured in step g) with astrocytes and pericytes.

22. A method of generating brain microvascular endothelial cells, comprising:

a) growing induced pluripotent stem cells (iPSCs) on a surface;

b) inducing differentiation of said stem cells by culturing said stem cells with unconditioned medium lacking bFGF under low oxygen conditions to produce endothelial cell (EC) regions of the culture;

c) expanding said EC region by culturing the cells in medium comprising retinoic acid, so as to produce brain microvascular endothelial cells (BMVECs);

d) seeding said BMVECs on a microfluidic device having flow;

e) exposing said seeded BMVECs to low oxygen conditions for at least 24 hours;

f) returning said BMVECs to normal oxygen tension; and g) culturing said BMVECs such that said BMVECs have increased expression of the transmembrane efflux pump protein ABCB as compared to normal oxygen conditions.

23. The method of claim 22, wherein said increased expression of said ABCB is approximately ten-fold.

24. The method of claim 22, wherein said low oxygen conditions of step b) and e) comprise 5% $O_2$ balanced with $N_2$.

25. The method of claim 22, wherein said seeded stem cells are co-cultured in step g) with astrocytes and pericytes.

26. A method of generating brain microvascular endothelial cells, comprising:

a) growing induced pluripotent stem cells (iPSCs) on a surface;

b) inducing differentiation of said stem cells by culturing said stem cells with unconditioned medium lacking bFGF under low oxygen conditions to produce endothelial cell (EC) regions of the culture;

c) expanding said EC regions by culturing the cells in medium comprising retinoic acid, so as to produce brain microvascular endothelial cells (BMVECs);

d) seeding said BMVECs on a microfluidic device having flow;

e) exposing said seeded BMVECs to low oxygen conditions for at least 24 hours;

f) returning said BMVECs to normal oxygen tension; and g) culturing said BMVECs such that said BMVECs form a barrier having a transendothelial electrical resistance (TEER) of over 2000 $\Omega$-cm$^2$ sustained for at least 3 days.

27. The method of claim 26, wherein said low oxygen conditions of step b) and e) comprise 5% $O_2$ balanced with $N_2$.

28. The method of claim 26, wherein said seeded stem cells are co-cultured in step g) with astrocytes and pericytes.

29. The method of claim 28, wherein TEER value is greater than 2500 $\Omega$-cm$^2$ at day three of culture.

30. The method of claim 28, wherein TEER value is greater than 2500 $\Omega$-cm$^2$ at day four of culture.

* * * * *